(12) United States Patent
Cherkaoui et al.

(10) Patent No.: US 6,746,729 B1
(45) Date of Patent: Jun. 8, 2004

(54) LIQUID CRYSTAL COMPOUNDS

(75) Inventors: Zoubair Mohammed Cherkaoui, Allschwil (CH); Carsten Benecke, Weil am Rhein (DE); Klaus Schmitt, Lörrach (DE)

(73) Assignee: Rolic AG, Zug (CH)

( * ) Notice: Subject to any disclaimer, the term of this patent is extended or adjusted under 35 U.S.C. 154(b) by 0 days.

(21) Appl. No.: 09/959,013

(22) PCT Filed: Apr. 11, 2000

(86) PCT No.: PCT/IB00/00448

§ 371 (c)(1),
(2), (4) Date: Oct. 17, 2001

(87) PCT Pub. No.: WO00/63154

PCT Pub. Date: Oct. 26, 2000

(30) Foreign Application Priority Data

Apr. 19, 1999 (GB) ................................................ 9908934

(51) Int. Cl.[7] ........................ C09K 19/20; C09K 19/32; C09K 19/30; C07C 69/74; C07C 69/76
(52) U.S. Cl. .............. 428/1.1; 252/299.61; 252/299.62; 252/299.63; 252/299.67; 560/55; 560/56; 560/85; 560/128
(58) Field of Search .................. 252/299.01, 299.61, 252/299.62, 299.63, 299.67; 428/1.1; 560/55, 56, 85, 128

(56) References Cited

U.S. PATENT DOCUMENTS 5,593,617 A * 1/1997 Kelly et al. ............ 252/299.67
6,136,225 A 10/2000 Meyer et al. .......... 252/299.01
6,379,758 B1 * 4/2002 Hanner et al. ................ 428/1.1
6,395,351 B1 * 5/2002 Benecke et al. ............. 428/1.1

FOREIGN PATENT DOCUMENTS

| DE | 19843724 | * 4/1999 |
| EP | 0 869 112 | 10/1998 |
| WO | WO 95/22586 | 8/1995 |
| WO | WO 97/00600 | 1/1997 |
| WO | WO 98/52905 | 11/1998 |

OTHER PUBLICATIONS

Derwent Abstract of WO 95/22586.
Derwent Abstract of WO 9700600.
Derwent Abstract of EP 0 869 112.

* cited by examiner

Primary Examiner—Shean C. Wu
(74) Attorney, Agent, or Firm—Finnegan, Henderson, Farabow, Garrett, & Dunner, L.L.P.

(57) ABSTRACT

Compounds of formula I:

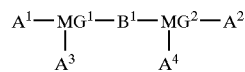

wherein the variables are defined as explained in the disclosure. The invention also provides liquid crystalline mixtures and optical or electro-optical devices including compounds of formula (I).

15 Claims, No Drawings

LIQUID CRYSTAL COMPOUNDS

This application is a national stage filing under 35 U.S.C. §371 of international application no. PCT/IB00/00448, filed on Apr. 11, 2000, which published in the English language. This application also claims the benefit of priority under 35 U.S.C. §119(a) to GB patent application no.9908934.4, filed on Apr. 19, 1999.

The invention relates to new liquid crystalline compounds, mixtures of those compounds and their application in optical and electro-optical devices. More particularly, it relates to the use of a component of a polymerisable liquid crystalline mixture in the production of orientated liquid crystalline polymers; compounds used as components in polymerisable liquid crystalline mixtures; liquid crystalline mixtures comprising these components; liquid crystalline polymers prepared from such components; and liquid crystalline devices comprising those compounds.

Liquid crystal polymers (LCPs) are used in the manufacture of optical components such as waveguides, optical gratings, filters, retarders, piezoelectric cells and non-linear optical cells and films. The choice of LCP for use in any one of these optical components depends upon its associated optical properties such as the optical anisotropy, refractive index, transparency and dispersion.

LCPs are manufactured by orientating a layer of a polymerisable liquid crystal single compound or mixture on an orientated substrate and cross-linking that layer to form a liquid crystal polymer (LCP) network. The configuration imposed by the orientation layer on the polymerisable LC single compound or mixture becomes fixed or frozen into the LCP network formed on cross-linking. The resulting LCP films are characterised by a high viscosity and are stable to mechanical stresses, temperature and light exposure. It is highly desirable that the polymerisable LC compounds used in the manufacture of the LCPs are chemically and thermally stable, stable to electromagnetic radiation, soluble in standard solvents and miscible with other LC components. The compounds should also exhibit liquid crystalline properties over the range 0 to 150° C., preferably 25 to 100° C.

Polymerisable liquid crystal compounds are known from EP 0 748 852, EP 0 700 981, EP 0 699 731, US 5 567 349, WO 97/00600, WO 98/52905 and WO 95/22586. These compounds are characterised by a relatively narrow liquid crystal range.

Materials comprising LCPs are generally prepared from a mixture of components, which includes at least one polymerisable LC single compound. The properties of the LCP material thus prepared depend upon the nature and properties of the components comprising the mixture. It is highly desirable that the components used in the preparation of the LCP materials are compatible. If the components of the mixture are incompatible, the corresponding mixtures may possess thermodynamic properties that make them unsuitable for use in LC devices. Incompatible LC mixtures are characterised by properties such as a depression of the clearing point, a reduction in the liquid crystalline range and problems in achieving a uniform orientation of the LCP material in the preparation of devices.

There is therefore a need for a liquid crystalline single compound or mixture which exhibits a broad liquid-cnrstalline thermal range and which can, alternatively or additionally, be orientated on a substrate prior to cross-linking in such a way that the orientation of the LC single compound or mixture on the substrate remains stable over the period required for manufacturing the LCP network.

There is also need for further liquid crystalline mixture components that are compatible with the other components of a liquid crystal mixture.

It has been surprisingly found that by using certain long chain compounds containing at least one mesogenic group, it is possible to prepare mixtures and materials having the ability to address, at least in part, the needs described above.

A first aspect of the invention provides a compound of formula I:

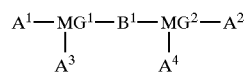

wherein $A^1$ to $A^4$ are independently selected from the group consisting hydrogen, a methyl group and a hydrocarbon group containing from 2 to 80 carbon atoms in which one or more carbon atoms are optionally replaced by a heteroatom selected from the group consisting —O—, —S—, and —N— with the proviso that firstly no two oxygen atoms are joined together and secondly that at least one of $A^1$ to $A^4$ includes a polymerisable group;

$B^1$ represents a hydrocarbon group containing from 4 to 80 carbon atoms, in which one or more carbon atoms are optionally replaced by a heteroatom selected from the group consisting —O—, —S—, and —N— with the proviso that no two oxygen atoms are joined together;

$MG^1$ and $MG^2$ are the same or different and each independently represents an aromatic or non-aromatic carbocyclic or heterocyclic ring system containing from 2 to 80 carbon atoms, with the proviso that firstly at least one of $MG^1$ and $MG^2$ comprises at least two ring systems and secondly when $MG^1$ and $MG^2$ are identical either $A^1$ and $A^2$ or $A^3$ and $A^4$ are different or at least three of $A^1$ to $A^4$ are different.

The compounds of the invention are chiral or achiral and preferably have a substantially linear backbone, the groups $A^1$, $MG^1$, $B^1$, $MG^2$ and $A^2$ being linearly arranged with respect to each other. It has been surprisingly found that the compounds of formula I can adopt a liquid crystalline mesophase over a broad thermal range. In addition they are characterised by melting points that are considerably lower than those of at least one of their mesogenic constituents. They are also valuable in the production of well-oriented LCP films having either a high or low optical birefringence and variable tilt.

For each of the groups $A^1$ to $A^4$, the term "hydrocarbon" is understood to include straight-chain and branched alkyl, alkenyl and alkynyl groups as well as cyclic groups. The terms "alkyl", "alkenyl" and "alkynyl" will accordingly be understood to include branched and straight chained groups. It will therefore be appreciated that one or more of the groups $A^1$ to $A^4$ may be selected from the group consisting of a $C_1$–$C_{20}$ alkyl, $C_1$–$C_{20}$ alkoxy, $C_1$–$C_{20}$ alkoxycarbonyl, $C_1$–$C_{20}$ alkylcarbonyl and a $C_1$–$C_{20}$ alkylcarbonyloxy group. Examples of $C_{1-20}$ alkyl groups that may be present in the compounds of the present invention include, without limitation, methyl, ethyl, propyl, butyl, pentyl, hexyl, heptyl, octyl, nonyl, decyl, undecyl, dodecyl and the like. Examples of $C_{1-20}$ alkoxy groups that may be present in the compounds of the present invention include, without limitation, methoxy, ethoxy, n-propoxy, isopropoxy, butoxy, pentyloxy, exyloxy, heptyloxy, octyloxy, nonyloxy, decyloxy, undecyloxy, dodecyloxy and the like. Examples of $C_1$–$C_{20}$ alkoxycarbonyl groups that may be present in the compounds of the present invention include, without limitation, methoxycarbonyl, ethoxycarbonyl, propoxycarbonyl, butoxycarbonyl, pentyloxycarbonyl, hexyloxycarbonyl, octyloxycarbonyl, nonyloxycarbonyl decyloxycarbonyl, undecyloxycarbonyl, dodecyloxycarbonyl and the like. Examples of $C_1$–$C_{20}$ alkylcarbonyl groups that may be present in the compounds of the present invention include, without limitation, acetyl, propionyl, butyryl, valeryl, hexanoyl, heptanoyl, octanoyl, nonanoyl, decanoyl, undecanoyl, dodecanoyl, terdecanoyl and the like. Examples of $C_1$–$C_{20}$alkylcarbonyloxy groups that may be present in the compounds of the present invention include, without limitation, acetoxy, propionyloxy, butyryloxy, valeryloxy, hexanoyloxy, heptanoyloxy, octanoyloxy, nonanoyloxy, decanoyloxy, undecanoyloxy, dodecanoyloxy, terdecanoyloxy and the like. Cyclic groups may contain up to 6 ring carbon atoms.

For the group $B^1$, the term "hydrocarbon" is understood to include straight-chain and branched alkylene, alkenylene and alkynylene groups. The terms "alkylene", "alkenylene" and "alkynylene" will be accordingly understood to include branched and straight chain groups.

Each of the hydrocarbon groups of $A^1$ to $A^4$ and $B^1$ are optionally substituted by a substituent selected from the group consisting of $C_{1-20}$ alkyl, $C_{2-20}$ alkenyl, $C_{2-20}$ alkynyl, $C_{4-20}$ aryl, $C_{3-20}$ cycloalkyl, $C_{3-20}$ cycloalkenyl, $C_{3-20}$ cycloalkynyl, amino, cyano, epoxy, halogen, hydroxy, nitro or oxo.

By the term "halogen" it should be understood to include fluorine, chlorine, bromine and iodine.

If a nitrogen containing group is used to replace one or more carbon atoms of the aforementioned hydrocarbon groups, this may be further substituted by a group selected from the group consisting of $C_{1-20}$ alkyl, $C_{2-20}$ alkenyl, $C_{2-20}$ alkynyl, $C_{4-20}$ aryl, $C_{3-20}$ cycloalkyl, $C_{3-20}$ cycloalkenyl and $C_{3-20}$ cycloalkynyl.

The groups $MG^1$ and $MG^2$ are optionally substituted by a substituent selected from the group consisting of $C_{1-20}$ alkyl, $C_{2-20}$ alkenyl, $C_{2-20}$ alkynyl, $C_{4-20}$ aryl, $C_{3-20}$ cycloalkyl, $C_{3-20}$ cycloalkenyl and $C_{3-20}$ cycloalkynyl, amino, cyano, epoxy, halogen, hydroxy, nitro and oxo.

In a first preferred embodiment of the first aspect of the invention, each or any of the groups $A^1$ to $A^4$ may be selected from a group of formula (II)

$$P\text{—}(Sp^1)_{k1}\text{—}(X^1)_{t1}\text{—} \quad\quad (II)$$

wherein

P is hydrogen or a polymerisable group selected from the group consisting $CH_2=CW$—, $CH_2=W$—O—, $CH_2=CW$—COO—, $CH_2=C(Ph)$—COO—, $CH_2=CH$—COO—Ph—, $CH_2=CW$—CO—NH—, $CH_2=C(Ph)$—CONH—, $CH_2=C(COOR')$—$CH_2$—COO—, $CH_2=CH$—O—, $CH_2=CH$—OOC—, (Ph)—CH=CH—, $CH_3$—C=N—$(CH_2)_{m3}$—, HO—, HS—, HO—$(CH_2)_{m3}$—, HS—$(CH_2)_{m3}$—, HO$(CH_2)_{m3}$COO—, HS$(CH_2)_{m3}$COO—, HWN—, HOC(O)—, $CH_2=CH$—Ph—$(O)_{m4}$

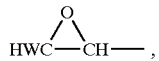, 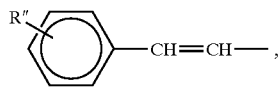,

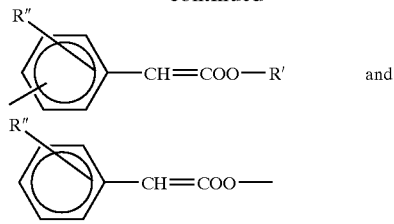

wherein

W is selected from the group consisting of H, F, Cl, Br, I and a $C_{1-5}$ alkyl group;
m3 is an integer having a value of from 1 to 9;
m4 is an integer having a value of 0 or 1,
R' represents a $C_{1-5}$ alkyl group; and
R" is selected from the group consisting of a $C_{1-5}$ alkyl group, methoxy, cyano, F, Cl, Br and I;
$Sp^1$ represents a $C_{1-20}$ alkylene group, in which one or more methylene groups are optionally replaced by a heteroatom selected from the group consisting of —O—, —S—, —N— or by linking groups such as —COO—, —OCO—, —CON— or by an aromatic or non-aromatic carbocyclic or heterocyclic ring system containing from 4 to 10 carbon atoms with the proviso that no two heteroatoms are joined together,
$k^1$ is an integer having a value of from 0 to 4;
$X^1$ is selected from the group consisting of —O—, —S—, —NH—, —N($CH_3$)—, —CH(OH)—, —CO—, —$CH_2$(CO)—, —SO—, —$CH_2$(SO)—, —$SO_2$—, —$CH_2$($SO_2$)—, —COO—, —OCO—, —OCO—O—, —S—CO—, —CO—S—, —SOO—, —OSO—, —SOS—, —$CH_2$—$CH_2$—, —$OCH_2$—, —$CH_2O$—, —CH=CH— and —C≡C—; and
$t^1$ is an integer having a value of 0 or 1;

The term —Ph— in formula (II) is used to represent 1,2-phenylene, 1,3-phenylene and 1,4-phenylene respectively. The term (Ph) in formula (II) is used to represent phenyl.

The $C_{1-20}$ alkylene group, $Sp^1$ is optionally substituted by one or more substituents selected from the group consisting F, Cl, Br, I and CN. In addition one or more of the $CH_2$ groups present in the hydrocarbon chain are optionally replaced by one or more groups selected from the group consisting of —O—, —S—, —NH—, —N($CH_3$)—, —CH(OH)—, —CO—, —$CH_2$(CO)—, —SO—, —$CH_2$(SO)—, —$SO_2$—, —$CH_2$($SO_2$)—, —COO—, —OCO—, —OCO—O—, —S—CO—, —CO—S—, —SOO—, —OSO—, —SOS—, —$SF_5$—, —C≡C—, —$(CF_2)_r$—, —$(CD_2)_s$—, —$(CCl_2)_s$— and $C(W^1)=C(W^2)$—, in which $W^1$ and $W^2$ are each independently selected from the group consisting of H, H-$(CH_2)_{q1}$— and Cl and with the proviso that no two heteroatoms are joined together. The integers r, s and q1 each independently represent a number of from 1 to 15.

It is preferred that the integers k1 and t1 each have a value of 1.

It is also preferred that $X^1$ is selected from the group consisting of —O—, —CO—, —COO—, —OCO—, —C≡C— and a single bond. It is especially preferred that $X^1$ is selected from the group consisting of —O—, —COO—, —OCO— and a single bond.

It is further preferred that $Sp^1$ is a straight-chain $C_{1-20}$ alkylene group. It is especially preferred that $Sp^1$ is selected from the group consisting of ethylene. propylene, butylene, pentylene, hexylene, heptylene, octylene, nonylene, decylene, undecylene, and dodecylene.

It is still further preferred that $P^1$ is selected from the group consisting of —$CH_2$=$CW^5$— or $CH_2$=$CW^5$—$(CO)_{v2}O$—, in which $W^5$ is selected from the group consisting of H, $CH_3$, F, Cl, Br and I and v2 is 0 or 1.

In a second preferred embodiment of the first aspect of the invention there are provided compounds of formula (I) in which the group $B^1$ is represented by the formula (III)

(III)

wherein

Sp$^2$ represents a $C_{4-20}$ alkylene group, in which one or more carbon atoms are optionally replaced by a heteroatom selected from the group consisting of —O— and —N— with the proviso that no two heteroatoms are joined together;

$X^2$ and $X^3$ are each independently selected from the group consisting of —O—, —S—, —NH—, —N($CH_3$)—, —CH(OH)—, —CO—, —$CH_2$(CO)—, —SO—, —$CH_2$(SO)—, —$SO_2$—, —$CH_2$($SO_2$)—, —COO—, —OCO—, —OCO—O—, —S—CO—, —CO—S—, —SOO—, —OSO—, —SOS—, —$CH_{12}$—$CH_2$—, —$OCH_2$—, —$CH_2O$—, —CH=CH—, —C≡C— and a single bond; and $t^2$ and $t^3$ each independently have a value of 0 or 1.

The compounds of the invention in which the group $B^1$ is represented by the formula (III) have been found to be particularly easy to synthesise.

The groups $X^2$ and $X^3$ are preferably each independently selected from the group consisting of —O—, —CO—, —COO—, —OCO—, —C≡C— and a single bond. It is especially preferred that the groups $X^2$ and $X^3$ are each independently selected from the group consisting of —O—, —COO—, —OCO— and a single bond.

The group Sp$^2$ is preferably a $C_{4-20}$ straight-chain alkylene group. It is especially preferred that Sp$^2$ is selected from the group consisting of propylene, butylene, pentylene, hexylene, heptylene, octylene, nonylene, decylene, undecylene and dodecylene.

In a third most preferred embodiment of the first aspect of the invention $B^1$ represents a group of formula (III) and at least one of $A^1$ to $A^4$ each independently represent a group of formula (II).

LCP materials prepared from the compounds of formula (I) have been found to be of particular use if they possess mesogenic properties. Such mesogenic properties may be achieved through the suitable choice of the groups $MG^1$ and $MG^2$. It is therefore preferred that at least one of the groups $MG^1$ and $MG^2$ has a mesogenic architecture.

It is preferred that at least one of the mesogenic groups $MG^1$ and $MG^2$ comprise at least two optionally-substituted aromatic or non-aromatic carbocyclic or heterocyclic ring systems. It is more preferred that one or both of $MG^1$ and $MG^2$ represents a mesogenic group comprising 1 to 4 aromatic or non-aromatic carbocyclic or heterocyclic ring systems having from 0 to 3 bridging groups, with the proviso that at least one of $MG^1$ and $MG^2$ includes at least two aromatic or non aromatic rings. $MG^1$ and $MG^2$ are optionally substituted by a group selected from the group consisting of $C_{1-20}$ alkyl, $C_{1-20}$ alkenyl, $C_{1-20}$ alkynyl and a polar group such as —$CF_3$, —$SF_5$, —$NO_2$, —CN, F, Cl, Br and I.

In a fourth preferred embodiment of the first aspect of the invention there are provided compounds in which the mesogenic groups $MG^1$ and $MG^2$ are represented by groups of formula (IV)

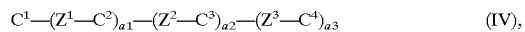
(IV), wherein $C^1$ to $C^4$ each independently represent a non-aromatic, aromatic, carbocyclic or heterocyclic group containing from 2 to 10 carbon atoms.

$Z^1$ to $Z^3$ are each independently selected from the group consisting of —CH(OH)—, —CO—, —$CH_2$(CO)—, —SO—, —$CH_2$(SO)—, —$SO_2$—, —$CH_2$($SO_2$)—, —COO—, —OCO—, —$COCF_2$—, —$CF_2CO$—, —S—CO—, —CO—S—, —SOO—, —OSO—, —SOS—, —$CH_2$—$CH_2$—, —OCH—, —$CH_2O$—, —CH=CH—, —C≡C—, —CH=CH—COO—, —OCO—CH=CH— and a single bond; and a1, a2 and a3 are each independently 0 or an integer having a value of from 1 to 3. with the proviso that a1+a2+a3≦3.

It is especially preferred that each of $C^1$ to $C^4$ are selected from the group consisting of

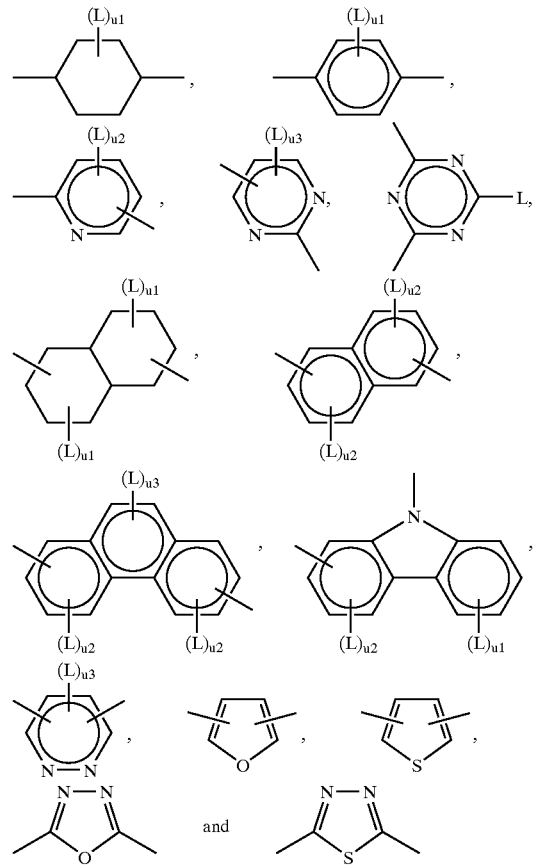

wherein

L is selected from the group consisting —$C_nH_{2n+1}$, —$C(O)C_nH_{2n+1}$, —$C(O)OC_nH_{2n+1}$, —$OC(O)C_nH_{2n+1}$, —$OC_nH_{2n+1}$, —$NO_2$, —CN, —$SF_5$ and halogen;

n represents an integer having a value of from 1 to 20;

u1 represents 0 or an integer having a value of from 1 to 4;

u2 represents 0 or an integer having a value of from 1 to 3; and u3 represents 0 or an integer having a value of from 1 to 2.

It is more especially preferred that $C^1$ to $C^4$ are each independently selected from the group consisting of optionally-substituted cyclohexyl, cyclohexylene, phenylene, phenyl, naphthyl, naphthylene, phenanthryl, phenanthrylene, decalinyl and decalinylene. Each of the groups $C^1$ to $C^4$ are optionally substituted by a group selected from the group consisting of $C_{1-20}$ alkyl, $C_{1-20}$ alkenyl, $C_{1-20}$ alkynyl and a polar group such as —$CF_3$, —$SF_5$, —$NO_2$, —CN, F, Cl, Br and I.

The compounds of the invention can be used to prepare devices containing a LCP material. It will be appreciated that the properties of a particular device will depend, in part, upon the nature of the compounds used to prepare the device. For example, materials having a high birefringence are generally required for the manufacture of retarder films or cholesteric filters having an elevated optical performance. LCP materials having a high birefringence can be readily prepared from compounds of formula (I) in which at least one of the groups $MG^1$ and $MG^2$ is highly birefringent. It has been found that a material with high birefringence can be prepared by using mesogenic groups that include at least two conjugated aromatic ring systems.

It is especially preferred that when materials having a high birefringence are required, each of the groups $C^1$ to $C^4$ are each independently selected from optionally-substituted phenyl, phenylene, naphthyl, naphthylene, phenanthryl and phenanthrylene; that a1, a2 and a3 are each independently 0 or an integer having a value of from 1 to 3; with the proviso that firstly $1<a1+a2+a3\leq3$, and secondly that when each of $C^1$ to $C^4$ are phenylene, $Z^1$ to $Z^3$ are each independently selected from the group consisting of —CH=CH—, —C≡C—, —CH=CH—COO—, —OCO—CH=CH— and a single bond. Each of the groups $C^1$ to $C^4$ are optionally substituted by a group selected from the group consisting of $C_{1-20}$ alkyl, $C_{1-20}$ alkenyl, $C_{1-20}$ alkynyl and a polar group such as —$CF_3$, —$SF_5$, —$NO_2$, —CN, F, Cl, Br and I.

Alternatively, there may be occasions where there is a requirement to use LCP materials having a low birefringence. It is, for example, preferred to use low birefringence LCP materials in the manufacture of optical polarisers characterised by short wave absorptions. Low birefringence LCP materials can be prepared from compounds of formula (I) having mesogenic groups $MG^1$ and $MG^2$ that contain no conjugated aromatic rings.

It is therefore especially preferred that, when materials having a low birefringence are required, the groups $C^1$ and $C^4$ are each independently selected from the group consisting of optionally-substituted phenyl, phenylene, cyclohexyl, cyclohexylene, decalinyl and decalinylene with the proviso that there are no directly connected phenyl or phenylene groups; that a1, a2 and a3 are each independently 0 or an integer having a value of from 1 to 3; with the proviso that firstly $1<a1+a2+a3\leq3$ and secondly when $C^1$ to $C^4$ are each phenyl or phenylene, $Z^1$ to $Z^3$ are each independently selected from the group consisting of —COO—, —OCO—, —$CH_2$—$CH_2$—, —$OCH_2$— and —$CH_2$—. Each of the groups $C^1$ to $C^4$ are optionally substituted by a group selected from the group consisting of $C_{1-20}$ alkyl, $C_{1-20}$ alkenyl, $C_{1-20}$ alkynyl and a polar group such as —$CF_3$, —$SF_5$, —$NO_2$, —CN, F, Cl, Br and I.

The compounds of the invention may be readily prepared using methods that are well known to the person skilled in the art, such as those documented in Houben-Weyl, *Methoden der Organischen Chemie,* Thieme-Verlag, Stuttgart. The compounds may for example be made according to the reaction schemes 1–6 in which the following abbreviations are used:

DEAD is Diethyl azodicarboxylate
TPP is Triphenylphosphine
THF is Tetrahydrofuran
DMF is N, N-Dimethylformamide
$Et_3N$ is Triethylamine
BTSS is Bis(trimethylsilyl)sulfate
DBU is 1,8-Diazabicyclo[5.4.0]undec-7-ene
EDC is N-(3-Dimethylaminopropyl)-N'-ethylcarbodiimide hydrochloride
DMAP is 4-Dimethylaminopyridine
$(PPh_3)_2PdCl_2$ is Bis(triphenylphosphine)palladium dichloride Scheme 1:

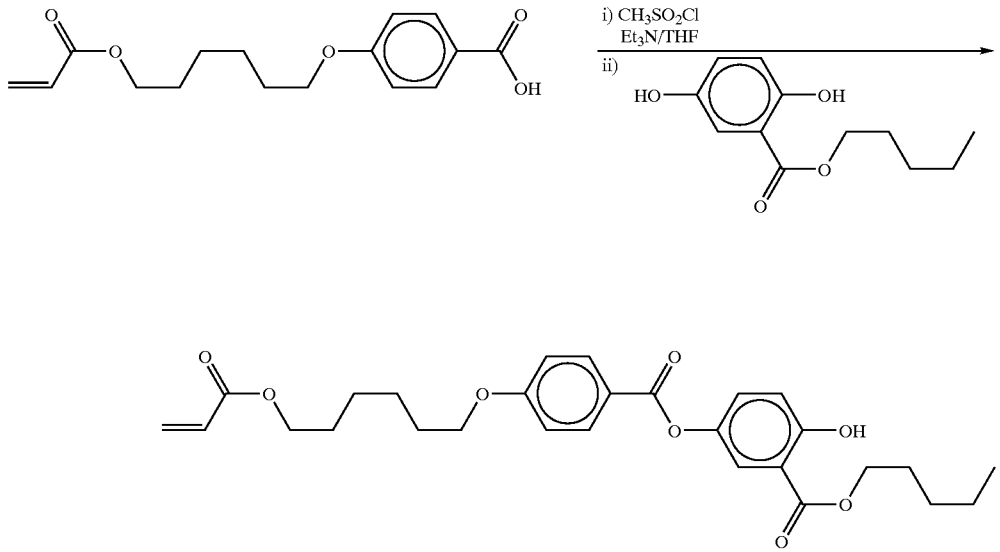

-continued
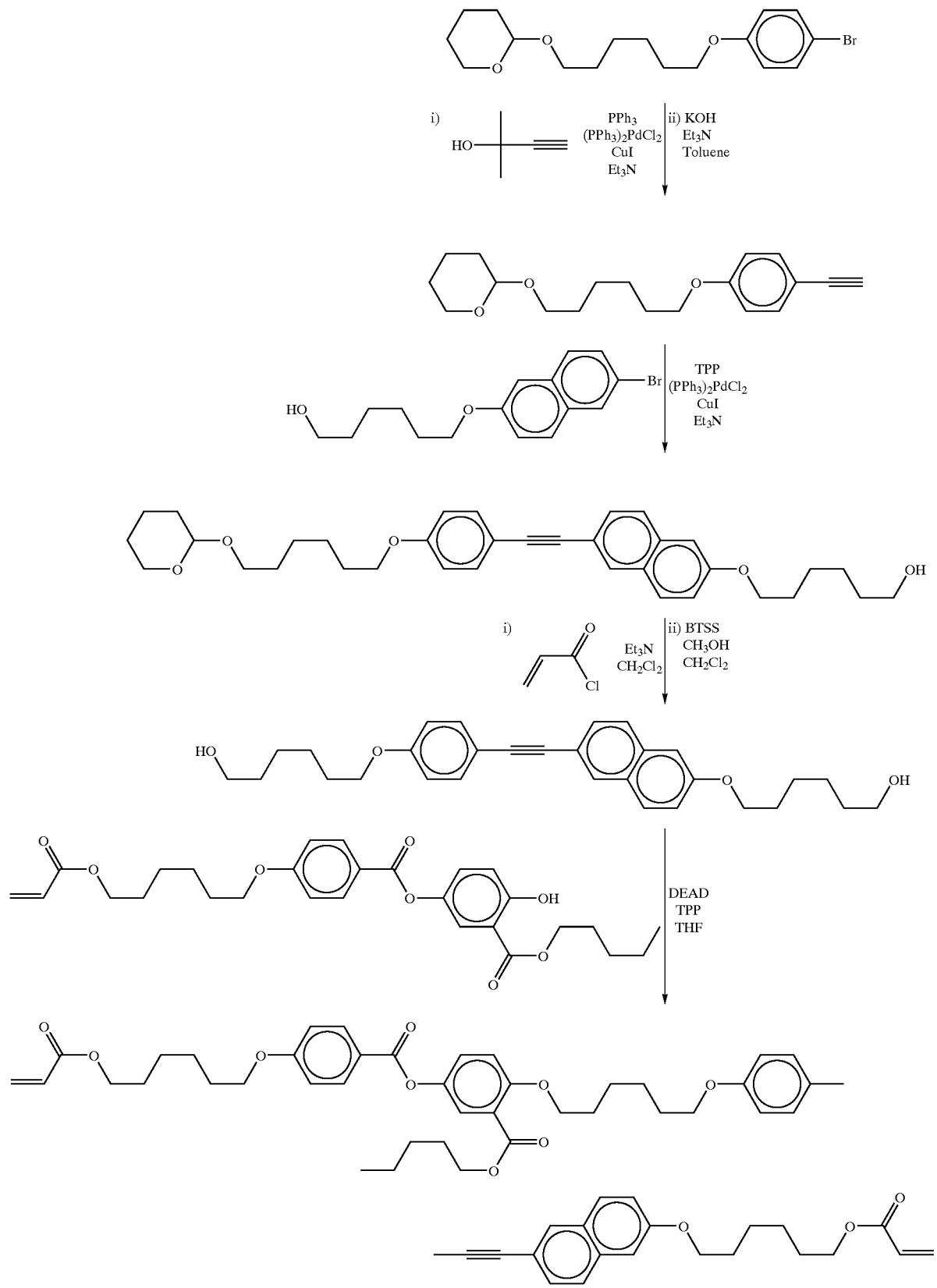

Scheme 2:
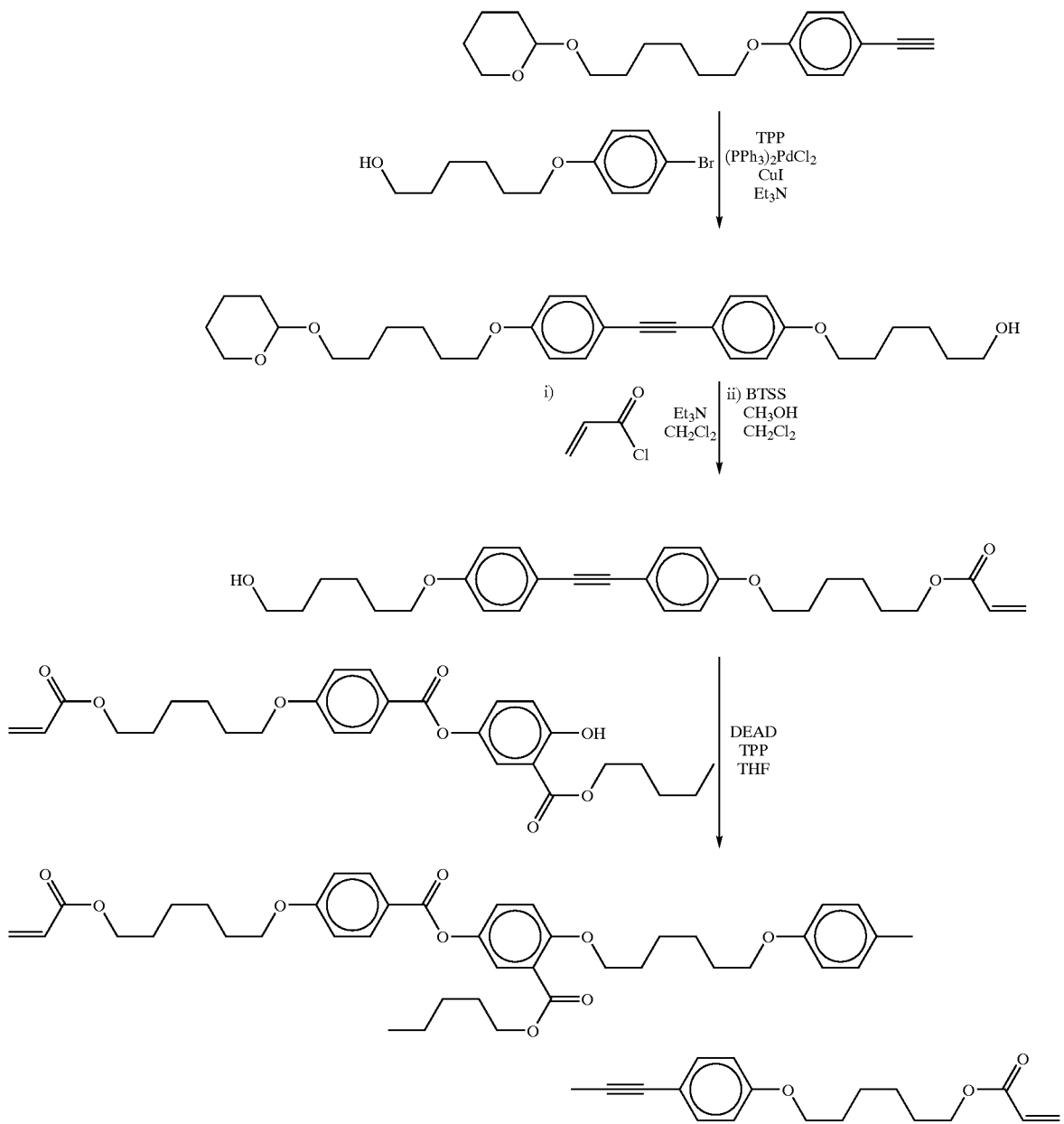
Scheme 3:
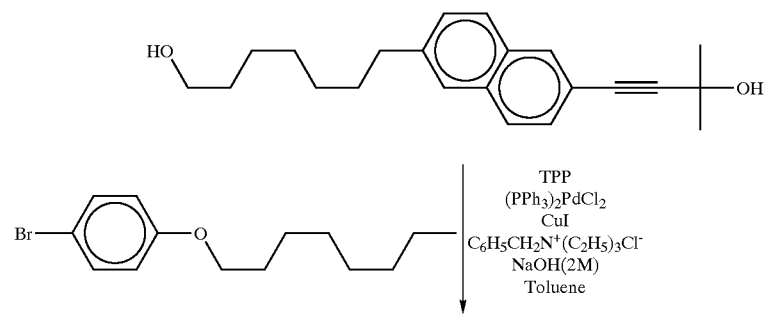

-continued
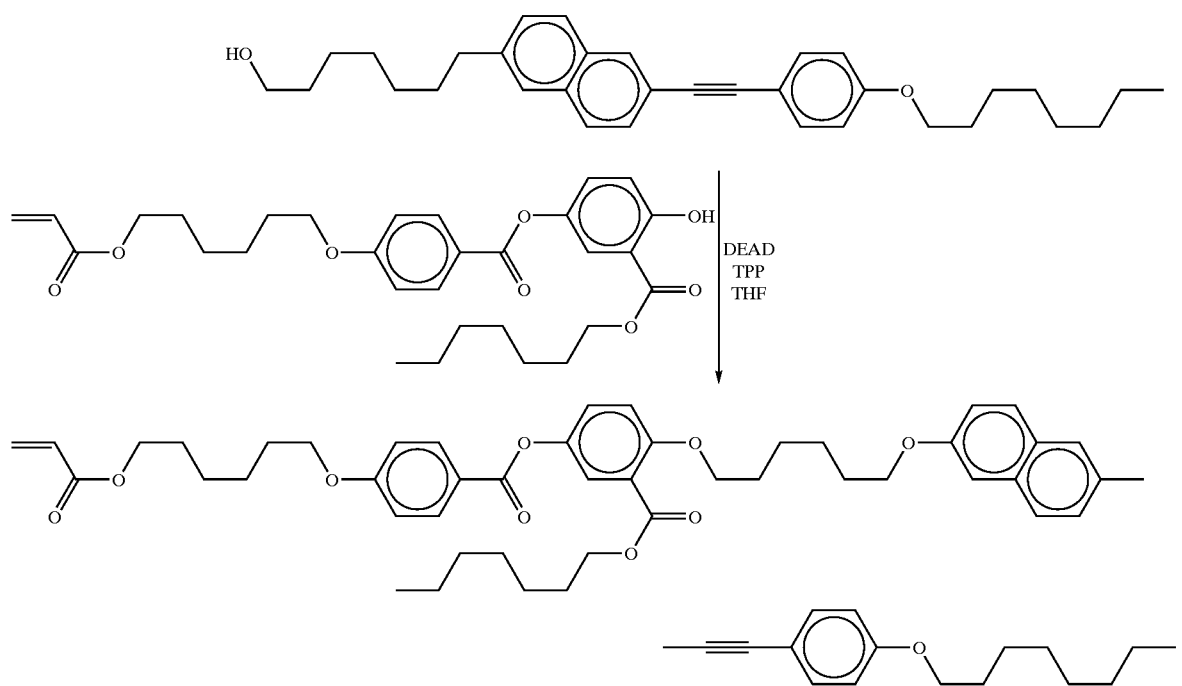
Scheme 4:
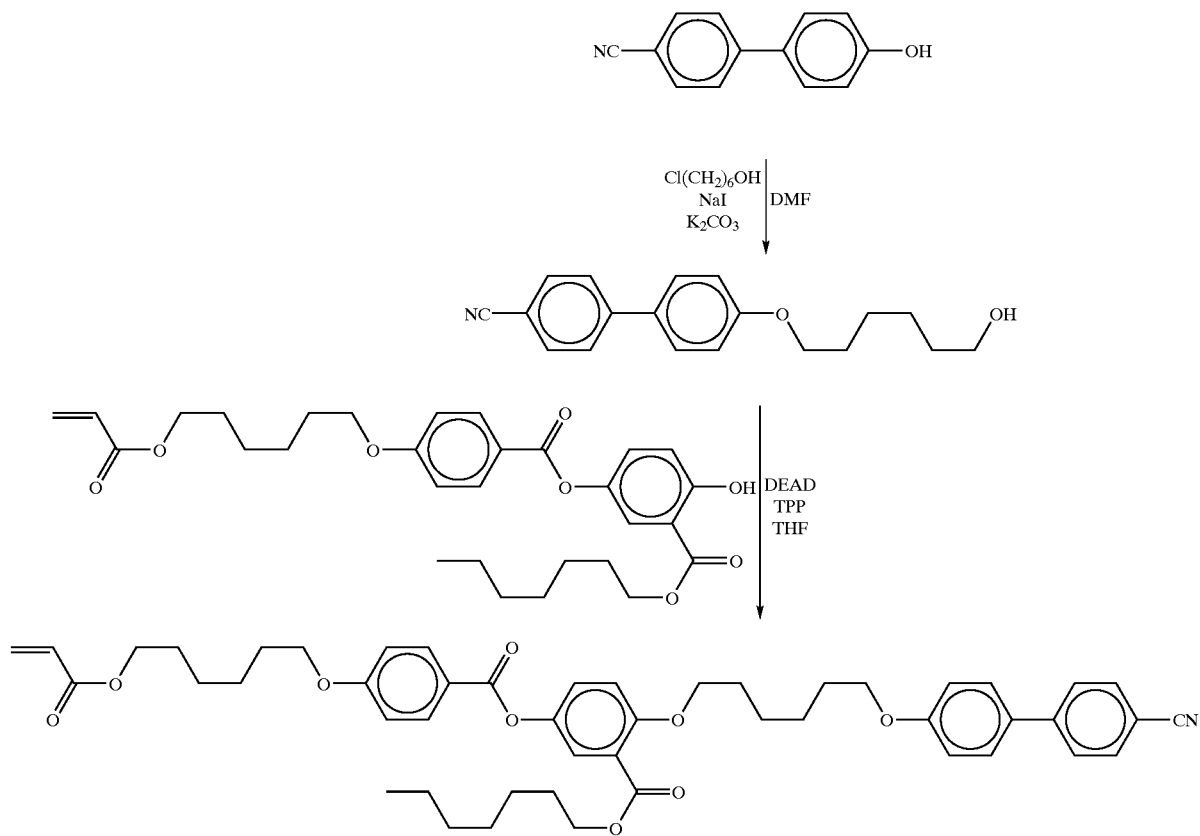

Scheme 5:
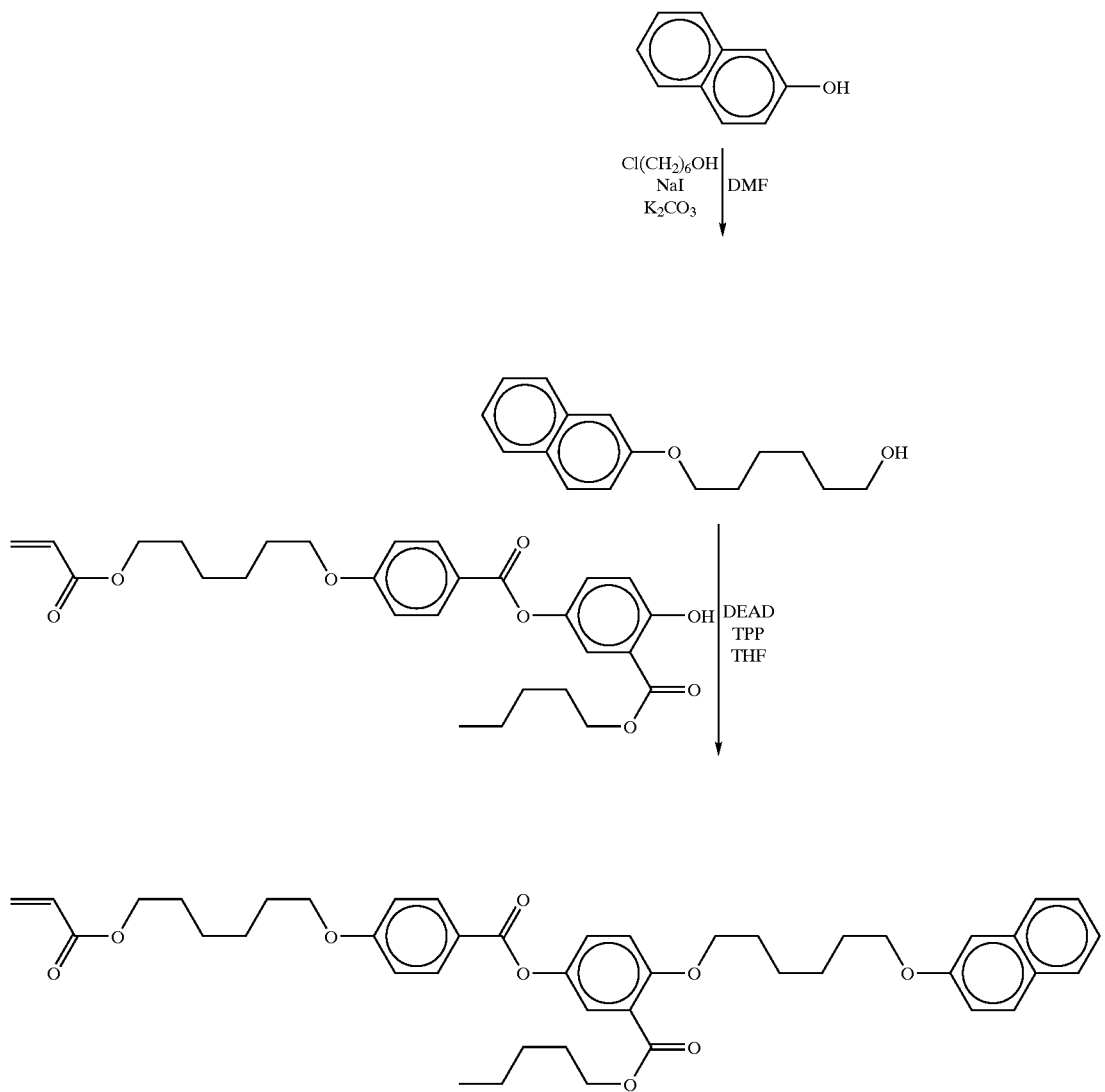
Scheme 6:
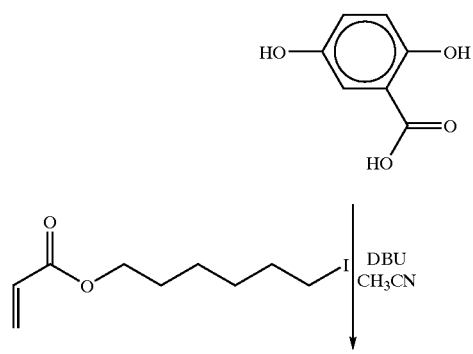

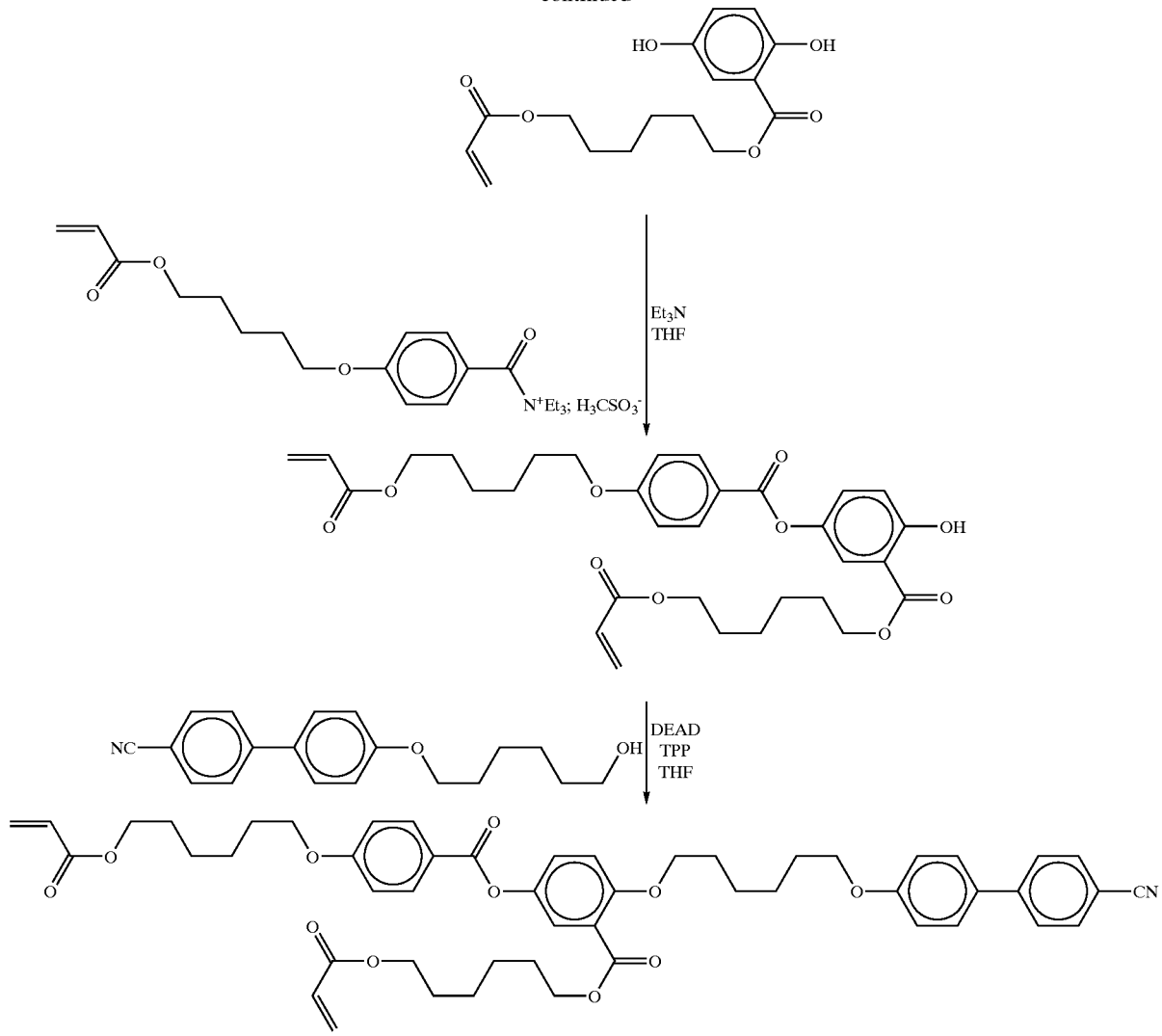
Examples of compounds that may be synthesised according to the preparative methods of Schemes 1–6 are given below. This list is provided merely by way of example and should not be understood as limiting the scope of the present invention:
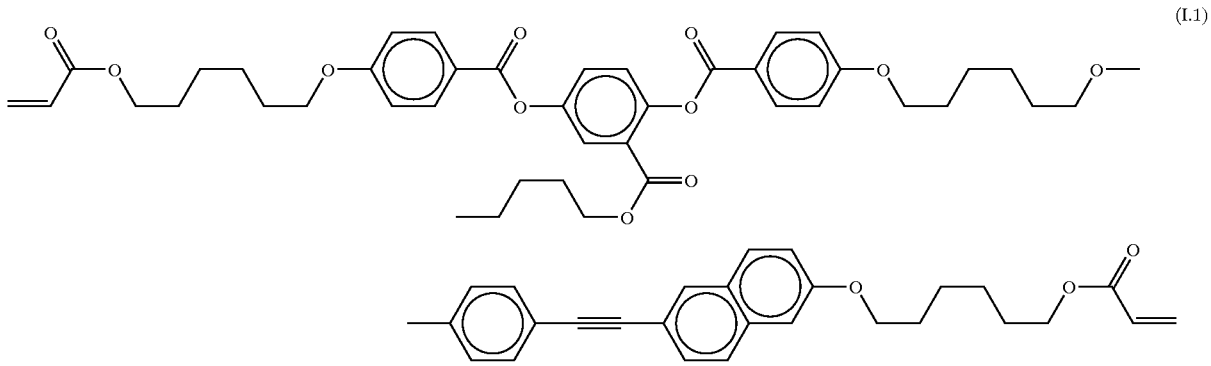

-continued
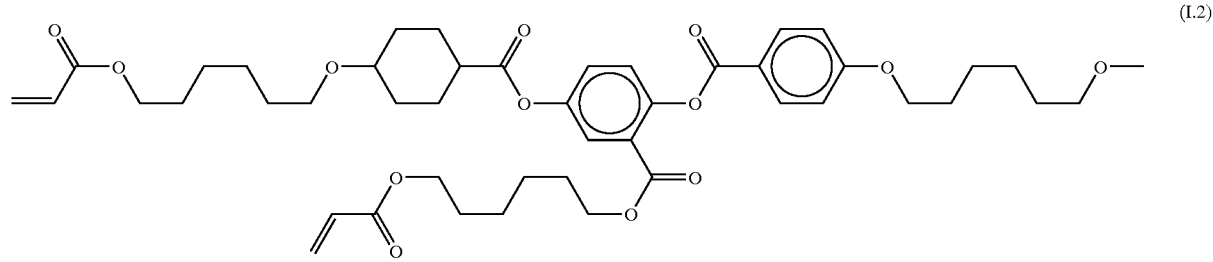
(I.2)
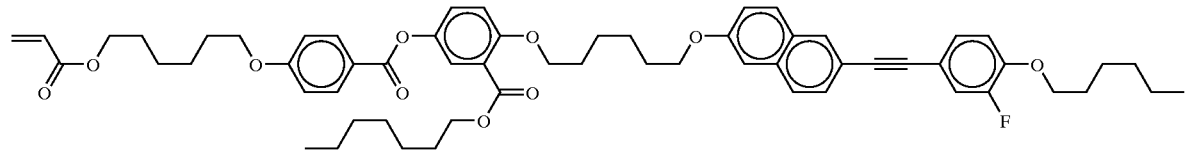
(I.3)
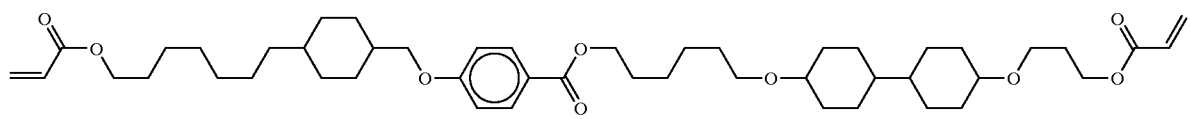
(I.4)
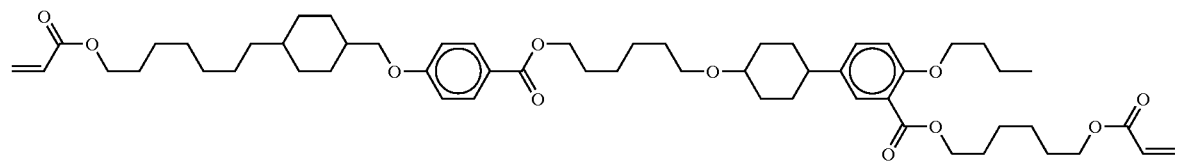
(I.5)
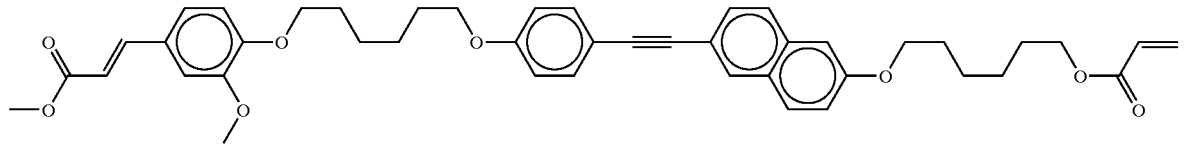
(I.6)
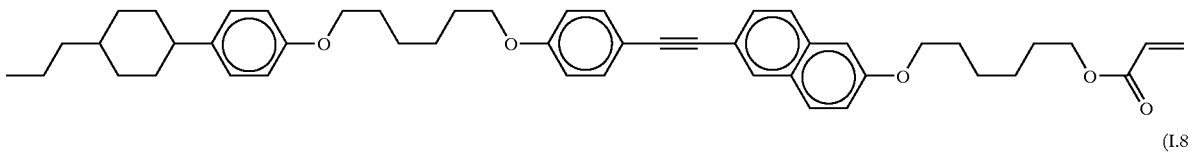
(I.7)
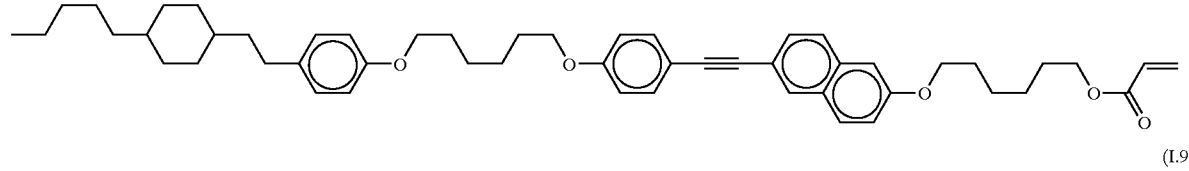
(I.8)
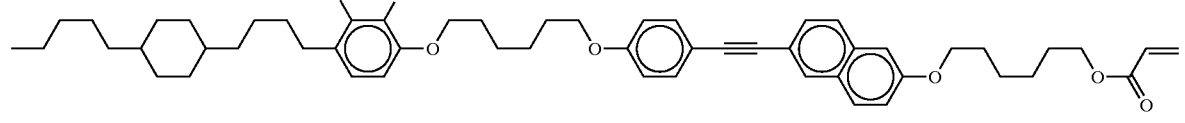
(I.9)

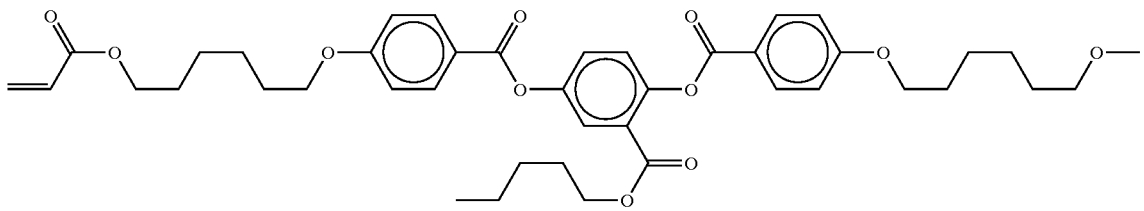

(I.10)

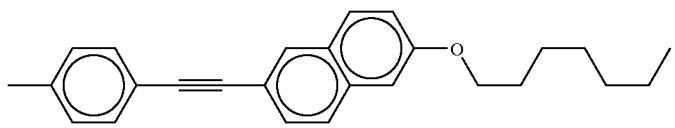

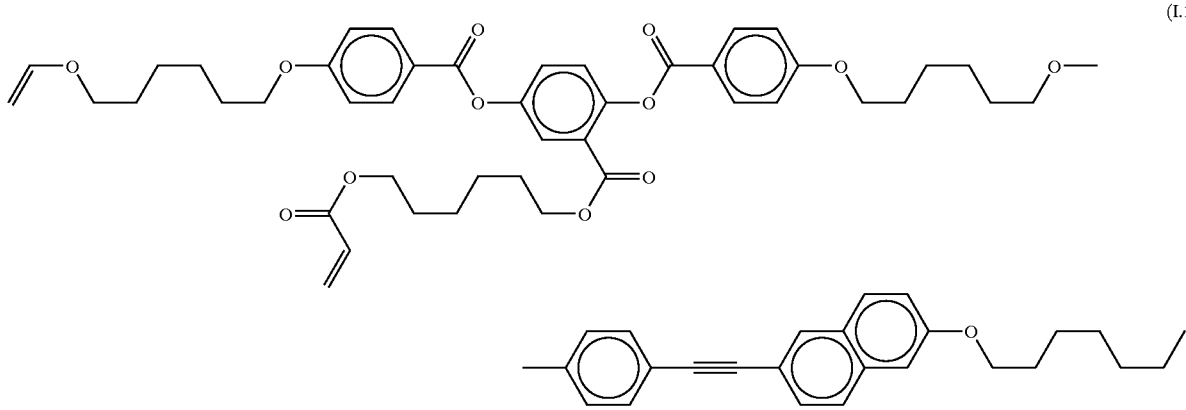

(I.11)

The compounds of formula I can be used alone or as a component of a liquid crystal mixture. Liquid crystalline materials comprising a compound of formula (I) may be used in the manufacture of LCPs. A second aspect of the present invention therefore comprises a liquid crystalline material comprising a compound of formula (I). A liquid crystalline material according, to the second aspect of the invention preferably comprises at least two components. The additional components must be miscible with the compound of formula (I) and may be selected from known mesogenic materials such as those reported in *Adv. Mater.* 5. 107 (1993), *Mol. Cryst. Liq. Crust.* 307, 111 (1997), *J. Mat. Chem.* 5, 2047 (1995) or in patent applications U.S. Pat. No. 5,593,617; U.S. Pat No. 5,567,349; GB-A-2 297 556; GB-A-2 299 333; DE-A-195 04 224; EP-A-0 606 940; EP-A-0 643 121 and EP-A-0 606 939 and are preferably selected from EP-A-0 606 940; EP-A-0 643 121 and EP-A-0 606 939.

Liquid crystal materials comprising a compound of formula (1) may be used in the form of a single compound, a liquid crystalline mixture, a (co)polymer, an elastomer, a polymer gel or a polymer network. The actual form of the liquid crystal material will depend upon the application in which it is to be used. Polymer networks have been found to be of particular use and in a first preferred embodiment of the second aspect of the invention there is provided a polymer network comprising a compound of formula (I). The polymer network preferably comprises at least two components, at least one of which is a compound of formula (I).

The polymer network can be prepared by the copolymerisation of a mesogenic mixture comprising:

i) at least one mesogenic polymerisable compound;

ii) at least one compound of formula (I); and iii) an initiator.

Polymer networks comprising a mesogenic polymerisable compound, a compound of formula (I) and an initiator may be used, for example, in the preparation of devices such as optical retarders. It will be appreciated that the components used in the preparation of the polymer network influence the properties of the network so prepared and that the choice of components will depend upon the application in which the polymer network is to be used. For example, in the preparation of devices such as cholesteric filters it is essential to include a chiral dopant as a component of the polymer network. A second embodiment of the second aspect of the invention therefore provides a polymer network comprising i) at least one mesogenic polymerisable compound, ii) at least one compound of formula (I);

iii) an initiator; and iv) one or more chiral dopants.

The mesogenic polymerisable compound is chiral or achiral and may be a compound of formula (I). Alternatively or in addition, the polymerisable compound may be selected from the known mesogenic materials referred to above. Preferably the polymerisable compound has a thermotropic sequence which includes a nematic phase.

The polymerisable mesogenic compound may be present in an amount comprising 0.01 to 99% by weight of the liquid crystalline polymer network mixture, preferably 50 to 95% by weight.

The polymerisable LC mixture or LCP network preferably comprises a compound of formula (I) in an amount from 0.1 to 100% by weight of the liquid crystalline mixture or network, preferably from 1 to 50% by weight.

The initiator is preferably a photoinitiator and may be a radical or cationic initiator that is present in an amount comprising 0.1 to 5% by weight of the polymer mixture, preferably from 0.2 to 2% by weight.

The polymer network may comprise further components. These include additional polymerisable compounds, stabilisers and dyes. The additional polymerisable compounds are preferably non-mesogenic and include at least one polymerisable functional group. Diacrylate and vinylate compounds are especially preferred.

Stabilisers suitable for use in liquid crystal mixtures of the present invention are those having the ability to prevent undesired spontaneous polymerisation during, for example, storage of the mixture. Examples of suitable commercially available stabilisers include 4-ethoxyphenol and 2,6-di-tert-butyl-4-methylphenol (BHT). The second aspect of the invention therefore includes liquid crystalline mixtures including a stabiliser.

It may be necessary to add a dye to the liquid crystalline mixture if, for example. colour filters are required. It is, however, preferred to prepare liquid crystalline mixtures containing no dye.

When the mixture further comprises a stabiliser, this is generally present in an amount comprising 0.01 to 5% by weight of the liquid crystalline mixture, preferably from 0.1 to 1% by weight.

These polymerisable liquid crystalline mixtures and materials may be formed into liquid crystalline polymer (LCP) films and a third aspect of the invention provides a LCP film comprising a compound of formula (I). LCP films may be readily prepared by UV polymerisation of a LC mixture according to the invention; a film comprising the LC mixture is formed on a substrate and polymerised using UV light to give a cross-linked liquid crystal polymer (LCP) film. The film is both light and temperature stable and can be used in the manufacture of devices such as waveguides, optical gratings, filters, retarders, piezoelectric cells or thin films exhibiting non-linear optical properties.

Examples of substrates used in the preparation of LCP networks include transparent substrates such as coated ITO (indium tin oxide), glass or plastic. Preferred substrates include glass or plastic, especially those including a layer of rubbed polyimide or polyamide or a layer of photo-oriented photopolymer (LPP). The preferred substrates greatly facilitate uniform orientation of the liquid crystalline mixture.

In the preparation of LCP films, it is particularly important to prevent the formation of defects or inhomogenities. This can be achieved by forming the polymerisable liquid crystalline mixture into a thin film; the mixture is placed between two of the aforementioned substrates, which were then sheared over a small distance until a planar order was obtained. Alternatively the mixture can be capillary filled between two of the said substrates. In each case the mixtures are then cured using, for example, UV light, preferably in the presence of a photoinitiator. Suitable photoinitiators are commercially available and are well known to a person skilled in the art.

The liquid crystalline mixtures and films of the present invention can be used to prepare optical and electro-optical devices. A fourth aspect of the invention provides an optical or electro-optical component containing a liquid crystalline polymer film comprising a compound of formula (I). The optical or electro-optical component may be a waveguide, an optical grating, a filter, a retarder, a piezoelectric cell or a non-linear optical cell or film.

The invention will now be described with reference to the following non-limiting examples. Variations on these falling within the scope of the invention will be apparent to a person skilled in the art.

In the following Examples the thermotropic phases are abbreviated as follows:
K crystalline
D discotic
S smectic
N nematic
N* chiral nematic (cholesteric)
I isotropic

EXAMPLE 1

5-[4-(6-Acryloyloxyhexyloxy)benzoyloxy]-2-[6-[4-[6-(6-acryloyloxyhexyloxy)-naphthalen-2-ylethynyl]phenoxy]hexyloxy]benzoic acid pentyl ester

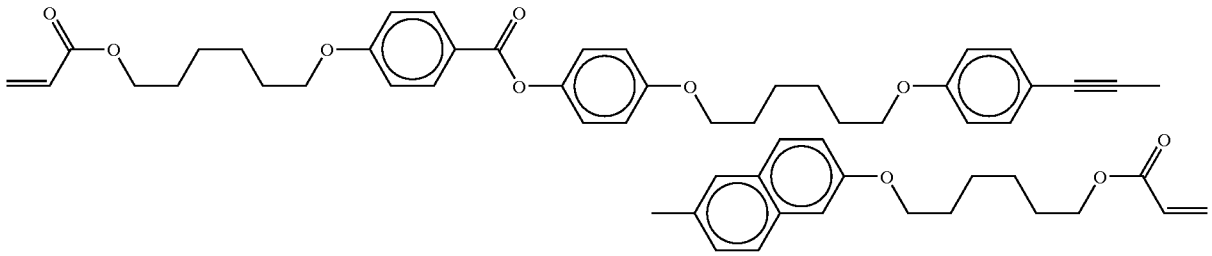

Preparation of 4-Bromo-1-[6-(tetrahydropyran-2-yloxy)hexyloxy]benzene

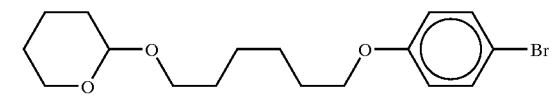

A mixture consisting of 4-bromophenol (20.75 g), 6-chloro-1-hexanol (20.50 g), potassium carbonate (33.20 g) and potassium iodide (21.9 g) in dimethylsulfoxide was stirred for 6 hours at 80° C. The reaction mixture was cooled and poured into 500 ml of water and extracted with 2×500 ml of ethyl acetate. The combined organic extracts were washed with saturated NaCl solution (3×100 ml) dried over magnesium sulfate and evaporated to dryness. This gave 37.4 g of a slightly beige oil of which 24.9 g were dissolved in 250 ml of dichloromethane containing 8.05 g of 3.4- dihydro-2H-pyran. The resulting solution was cooled to 5° C. A solution of bis-trimethylsilyl sulfate (0.38 g) in 10 ml of dichloromethane was then added dropwise the reaction mixture. The resulting mixture was stirred for two hours at 5° C. Triethylamine (4 ml) was added to the reaction mixture and stirring was continued for one hour at room temperature. The reaction mixture was then poured into 300 ml of water and extracted with dichloromethane (2×300 ml). The combined organic extracts were dried over magnesium sulfate and evaporated to dryness to give 33.95 g of a slightly beige residue, which was then filtered through a silica gel column using a cyclohexane/ethyl acetate (8/2) as eluent to give 28.9 g of 4-bromo-1-[6-(tetrahydropyran-2-yloxy)hexyloxy] benzene as colourless oil.

Preparation of 4-[6-(Tetrahydropyran-2-yloxy) hexyloxy]phenyl acetylene

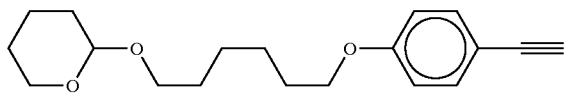

A degassed mixture of 4-bromo-1-[6-(tetrahydropyran-2-yloxy)hexyloxy]benzene (20 g), 2-methyl-3-butyn-2-ol (18.85 g), triphenylphosphine (TPP, 0.59 g), copper (I) iodide (0.11 g) and bis(triphenylphosphine)palladium dichloride (0.40 g) in 200 ml of triethylamine was refluxed for 4 hours under an atmosphere of argon. After being cooled the reaction mixture was filtered over celite to give a yellowish solution which was evaporated to dryness. The resulting yellow oil was dissolved in 200 ml of a toluene/triethylamine mixture (1:1) to which 14.45 g of KOH was then added. The resulting mixture was heated at reflux for 12 h, cooled and filtered over 260 g of silica gel using diethylether as eluent. This yields a dark oil which was purified by chromatography using a silica gel clolumn and cyclohexane/ethyl acetate (9:1) as eluent to give 12.28 g of 4-[6-(tetrahydropyran-2-yloxy)hexyloxy]phenylacetylene as a red oil.

Preparation of 6-(6-Bromo-naphthalen-2-yloxy)-hexan-1-ol

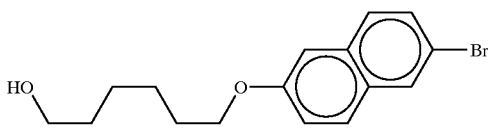

A mixture of 6-bromo2-naphthol (22.30 g), 6-chloro-1-hexanol (20.50 g), potassium carbonate (20.50 g) and potassium iodide (1.50 g) in dimethylformamide (DMF, 100 ml) was heated at 100° C for 4 h. The mixture was then cooled and poured into 150 ml of HCl (3N) and extracted with ether (3×200 ml). The combined ether extracts were washed with saturated NaCl solution (200 ml), dried over magnesium sulfate, evaporated to give a brownish oil and filtered through a silica gel column (150 g,) using dichloromethane as eluent to give a brownish solid. The brown solid was recrystallised from hexane/dichloromethane (9/1) to give 24.8 g of 6-(6bromo-naphthalen-2-yloxy)hexan-1-ol as white needles.

Preparation of 6-[6-[4-[6-(Tetrahydropyran-2-yloxy) hexyloxy]phenylethynyl]-naphthalen-2-yloxy]hexan-1-ol

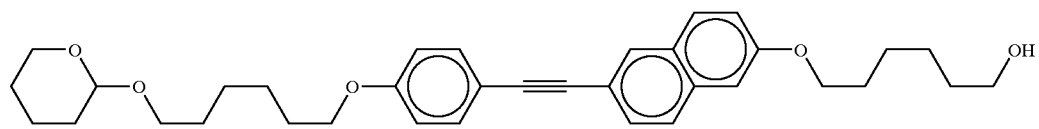

A degassed mixture of pure 6-(6-bromonaphthalen-2-yloxy)hexan-1-ol (5.88 g), 4-[6-(tetrahydropyran-2-yloxy) hexyloxy]phenyl acetylene (6.05 g), triphenylphosphine (0.21 g), copper(I) iodide (0.04 g) and bis (triphenylphosphine)palladium dichloride (0.14 g) in 60 ml of triethylamine was refluxed for 2 hours under an atmosphere of argon. The reaction mixture was cooled and filtered though celite to give a yellowish solution which was then evaporated to dryness to give a yellow residue, which was purified by chromatography using a silica gel column and cyclohexane/ethyl acetate (2:1, 1:1) as eluent, followed by recrystallisation of the resulting solid from cyclohexane/ ethyl acetate (100 ml/3 ml) to give 5.10 g of 6-[6-[4-[6-(tetra-hydropyran-2-yloxy)hexyloxy]phenylethyny] naphthalen-2-yloxy]hexan-1-ol as a white powder.

Preparation of Acrylic acid 6-[6-[4-[6-(tetrahydropyran-2-yloxy)hexyloxy]phenyl-ethynyl] naphthalen-2-yloxy]hexyl ester

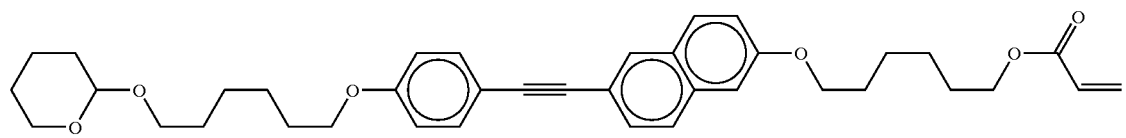

To a stirred solution 6-[6-[4-[8-(tetrahydropyran-2-yloxy) hexyloxy]phenylethynyl]-naphthalen-2-yloxy]hexan-1-ol (4.05 g) and triethylamine (0.89 g) in dichloromethane (50 ml) at 5° C. a solution of acroyl chloride (0.73 g) in dichloromethane (2 ml) was added dropwise. Upon complete addition, the reaction mixture was stirred at room temperature for 1 h, poured into 100 ml of water and extracted with dichloromethane (3×30 ml). The combined organic extracts were washed with saturated NaCl solution (100 ml) and dried over magnesium sulfate. The solvent was removed under reduced pressure to give a yellow oil, which was purified by flash chromatography through a silica-gel column using cyclohexane/ethyl acetate (2:1) as eluent to give 3.69 g of acrylic acid 6-[6-[4-[6-(tetrahydropyran-2-yloxy)hexyloxy]phenylethynyl]-naphthalen-2-yloxy]hexyl ester as a white crystalline material.

Preparation of Acrylic acid 6-{6-[4-(6-hydroxyhexyloxy)phenylethynyl]-naphthalen-2-yloxy)hexyl ester

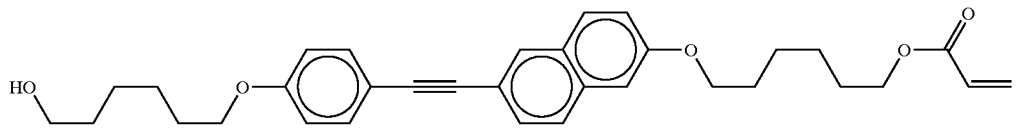

A solution of 6-[6-[4-[6-(tetrahydropyran-2-yloxy)hexyloxy]phenylethynyl]-naphthalen-2-yloxy]hexyl ester (3.65 g) and bis(trimethylsilyl)sulfate (0.05 g) in methanol/dichloromethane (50 ml/20 ml) was stirred at 60° C. for 90 min. Removal of the solvent gave a residue which was then recrystallised from cyclohexane/ethyl acetate (9:1) to give 2.11 g of acrylic acid 6-{6-[4-(6-hydroxyhexyloxy)-phenylethynyl]naphthalen-2-yloxy)hexyl ester as a white crystalline material.

Preparation of 5-[4-(6-Acryloyloxyhexyloxy)benzoyloxy]-2-hydroxybenzoic acid pentyl ester

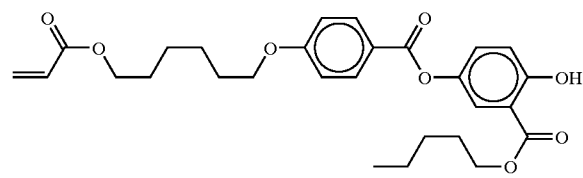

A solution of mesyl chloride (7.45 g) in 50 ml of dry THF was added in a dropwise fashion (over a period of 15 min) to a solution of 4-[(6-acryloyloxyhexyloxy)-benzoyloxy)]benzoic acid (19.00 g) and triethylamine (26.3 g) in 600 ml of dry THF, cooled at −25° C. and maintained and under argon atmosphere. Upon complete addition, the reaction mixture was further stirred for 45 min at −25° C. treated with a solution of 2,5-dihydroxybenzoic acid pentyl ester in 50 ml of dry THF, further stirred at −25° C for 30 min and then stirred at room temperature for 90 min. The reaction mixture was poured into 265 ml of HCl (3N) and extracted with 3×200 ml of ether. The combined organic extracts were washed with a half saturated NaCl solution (500 ml), dried over MgSO$_4$ and evaporated to dryness to give a slightly yellow oil which was purified by flash column chromatography using a short silica column and cyclohexane/ dichloromethane (2/1) as eluent to give 19.65 g of 5-[4-(6-acryloyloxy-hexyloxy)benzoyloxy]-2-hydroxybenzoic acid pentyl ester as colourless oil.

Preparation of 5-[4-(6Acryloyloxyhexyloxy) benzoyloxy]-2-[6-[4-6-(6-acryloyl oxyhexyloxy) naphthalen-2-ylethynyl]phenoxy]hexyloxy]benzoic acid pentyl ester

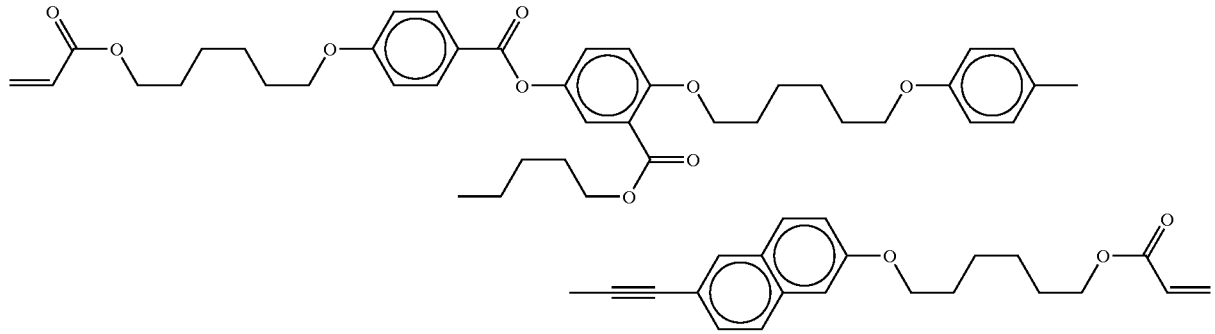

To a stirred solution of acrylic acid 6-{6-[4-(6-hydroxyhexyloxy)phenylethynyl]-naphthalen-2-yloxy) hexyl ester (1.05 g), 5-[4-(6-acryloyloxyhexyloxy) benzoyloxy]-2-hydroxybenzoic acid pentyl ester (1.12 g) and triphenylphosphine (0.59 g) in tetrahydrofuran (20 ml) was added under argon and in a dropwise fashion diethyl azodicarboxylate (DEAD, 0.39 g). Upon complete addition, the reaction mixture was stirred at room temperature overnight, and the solvent was then removed under reduced pressure to give a residue which was purified by flash chromatography using a silica-gel column and cyclohexane/ ethyl acetate (8/2) as eluent to give 0.66 g of 5-[4-(6-acryloyloxyhexyloxy)benzoyloxy]-2-[6-[4-[6-(6-acryloyloxyhexyloxy)naphtha len-2-ylethynyl]phenoxy] hexyloxy]benzoyloxy]benzoic acid pentyl ester as white crystalline material. K 39° C. N 113° C. I.

EXAMPLE 2

5-[4-(6-Acryloyloxyhexyloxy)benzoyloxy]-2-[6-(4'-cyanobiphenyl4-yloxy)-hexyloxy]benzoic acid 6-acryloyloxy hexyl ester

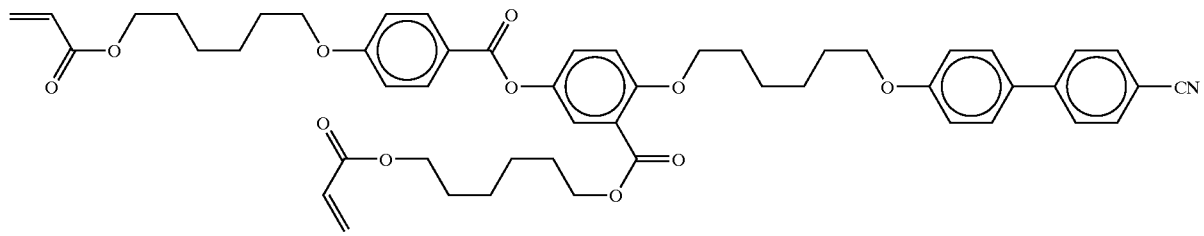

Preparation of 2,5-Dihydroxybenzoic acid-6-acryloyloxy hexyl ester

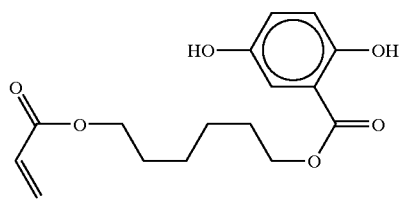

To a stirred solution of 2,5-dixydroxybenzoic acid (11.56 g) and acrylic acid-6-iodohexyl ester (22.57 g) in acetonitrile (250 ml) was added 1,8-Diazabicyclo[5,4,0]undec-7-ene (11.42 g). The reaction mixture was heated at reflux for 2 h. The reaction mixture was cooled to room temperature, poured into 200 ml of HCl (3N) and extracted with ether (2×250 ml). The combined organic extracts were washed with saturated NaCl solution (200 ml), dried over magnesium sulfate and evaporated to dryness. The resulting dark-yellow oil was filtered through a short silica-gel column (50 g, $CH_2Cl_2$) to give 25.5 g of 2,5-dihydroxybenzoic acid 6-acryloyloxyhexyl ester as slightly yellow oil.

Preparation of 5-[4-(6-Acryloyloxyhexyloxy)benzoyloxy]-2-hydroxybenzoic acid 6-acryloyloxyhexyl ester A solution of mesyl chloride (3.44 g) in 50 ml of dry THF was added dropwise under argon to a cooled (−25° C.) solution of 4-(6-acryloyloxyhexyloxy)benzoic acid (8.35 g) and triethylamine (6.07 g) in 100 ml of dry THF. After complete addition (15 min), the reaction mixture was stirred for a further 30 min at −25° C., treated with a solution of 2,5-dihydroxybenzoic-6-acryloyloxyhexyl ester in 50 ml of dry THF and further stirred at −25° C. for 4 h. The reaction mixture was then filtered through celite and the solvent was removed by evaporation. The filtrate was purified by flash chromatography using a short silica-gel column and dichloromethane/diethylether (39/1) as eluent to give 10.8 g of 5-[4-(6-acryloyloxyhexyloxy)benzoyloxy]-2-hydroxybenzoic acid 6-acryloyloxyhexyl ester as a slightly beige oil.

Preparation of 5-[4-(6-Acryloyloxyhexyloxy)benzoyloxy]-2-[6-(4'-cyano-biphenyl-4-yloxy)hexyloxy]benzoic acid 6-acryloyloxyhexyl ester

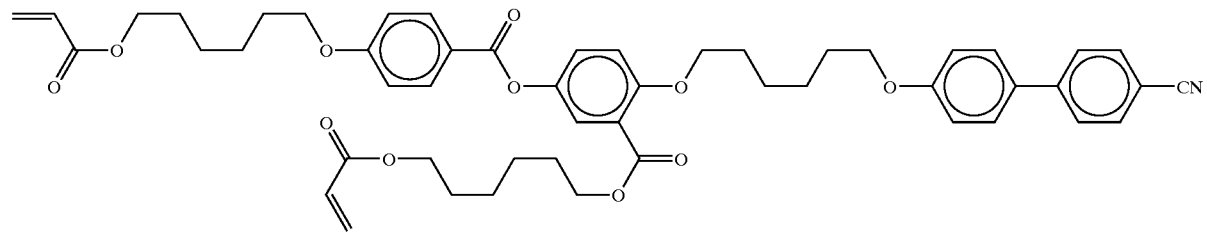

Following the procedure described in Example 2(2), a reaction mixture comprising 6-(4'-cyanobiphenyl-4-yloxy)hexan-1-ol (2.95 g), 5-[4-(6-acryloyloxyhexyloxy)- benzoyloxy]-2-hydroxybenzoic-6-acryloyloxy hexyl ester (5.83 g), triphenylphosphine (3.67 g) and diethyl azodicarboxylate (2.09 g) in 100 ml of dry THF, gave, upon purification through a silica-gel column, using ethyl acetate/cyclohexane (1/3) as eluent, 5.6 g of the desired compound as white crystalline material. K 71° C. N 77° C. I.

The nematic phase was maintained at room temperature upon cooling of the sample from the isotropic state.

EXAMPLE 3

Acrylic acid 6-{6-[4-(6-{4-[2-(trans-4-pentylcyclohexyl)ethyl]phenoxy}hexyloxy)-phenylethynyl]naphthalen-2-yloxy}hexyl ester

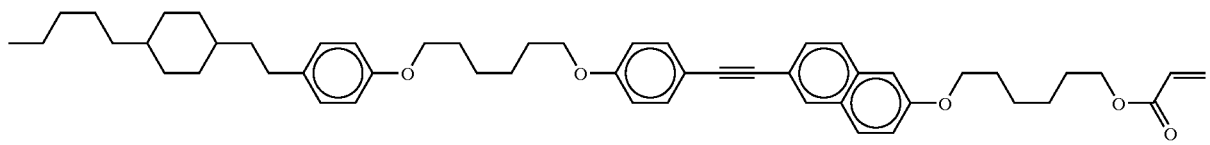

Following the procedure described in Example 2(2), a reaction comprising acrylic acid 6-{6-[4-(6-hydroxyhexyloxy)phenylethynyl]naphthalen-2-yloxy}hexyl ester (1.03 g), 1-(4-hydroxyphenyl)-2-(trans-4-pentylcyclohexyl)ethane (0.53 g), triphenylphosphine (0.63 g) and diethyl azodicarboxylate (0.38 g) in 20 ml of dry

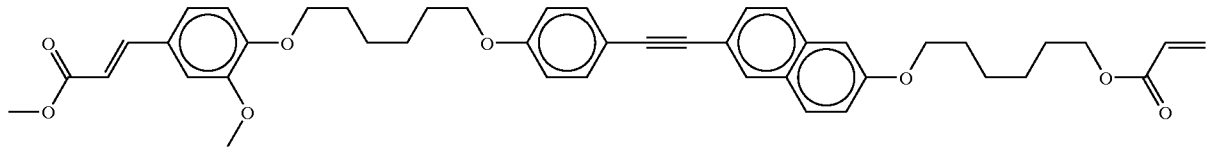

THF, gave, upon purification on silica-gel column using dichloromethane as eluent, 0.72 g of the desired compound as white crystalline material. K 118° C. N 130° C. I.

EXAMPLE 4

Acrylic acid 6-{6-[4-(6-{4-[3-trans-4-pentylcyclohexyl)propyl-1-oxy]-2,3-difluoro-phenoxy}hexyloxy)phenylethynyl]naphthalen-2-yloxy}hexyl ester

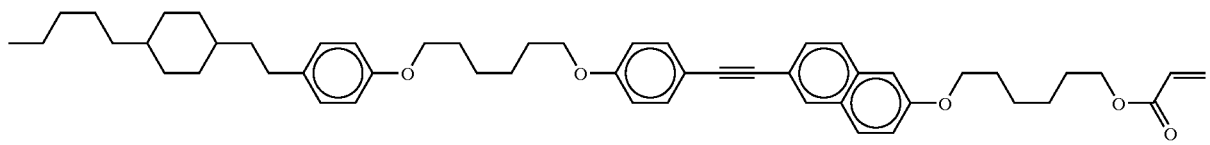

Following the procedure described in Example 2(2), a reaction mixture comprising acrylic acid 6-{6-[4-(6-hydroxyhexyloxy)phenylethynyl]naphthalen-2-yloxy}hexyl ester (1.03 g), 1-(2,3-difluoro-4-hydroxyphenoxy)-3-(trans-4-pentylcyclohexyl)-propane (0.68 g), triphenylphosphine (0.63 g) and diethyl azodicarboxylate (0.38 g) in 20 ml of dry THF, gave upon purification through a silica-gel column, using dichloromethane as eluent, 0.82 g of the desired compound as white crystalline material. K 98° C. N 119° C. I.

EXAMPLE 5

(E)-3-{4-[6-(4-[6-(Acryloyloxyhexyloxy)naphthalen-2-ylethynyl]phenoxyl)hexyloxy ]-3-methoxyphenyl}acrylic acid methyl ester

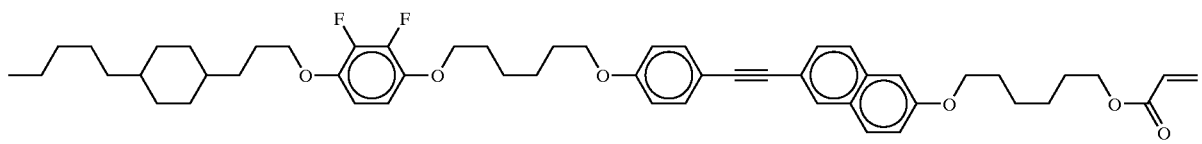

Following the procedure described in Example 2(2), a reaction mixture comprising acrylic acid 6-{6-[4-(6-hydroxyhexyloxy)phenylethynyl]naphthalen-2-yloxy}hexyl ester (1.03 g), (E)-3-(4-hydroxy-3-methoxyphenyl)acrylic acid methyl ester (0.42 g), triphenylphosphine (0.52 g) and diethyl azodicarboxylate (0.35 g) in 30 ml of dry THF, gave upon purification using a silica-gel column and ethyl acetate/cyclohexane (1/2) as eluent, 1.12 g of the desired compound as white crystalline material. K 103.5° C. S 106.8° C. N 127° C. I.

EXAMPLE 6

The following compounds are readily oriented in their liquid-crystalline phase(s) when they are filled by capillarity, in the isotropic state, into polyimide coated cells with thickness of 2 to 20 μm. Their corresponding phase transition temperatures obtained by cooling from the isotropic state and measured by optical microscopy, are listed:

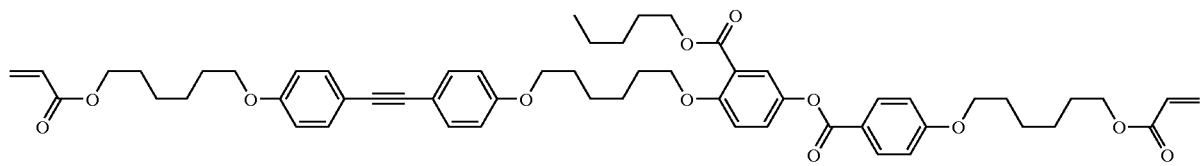
Iso. 89° C. N 23° C. K
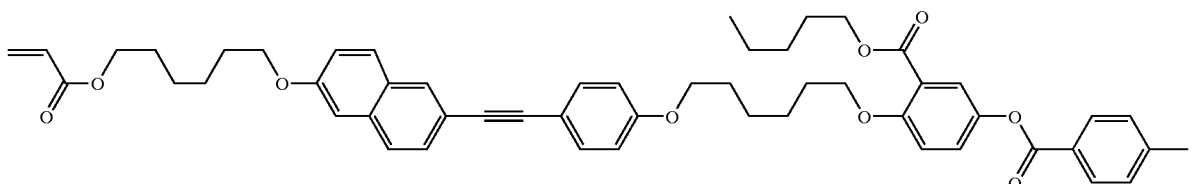
Iso. 113° C. N 23° C. K
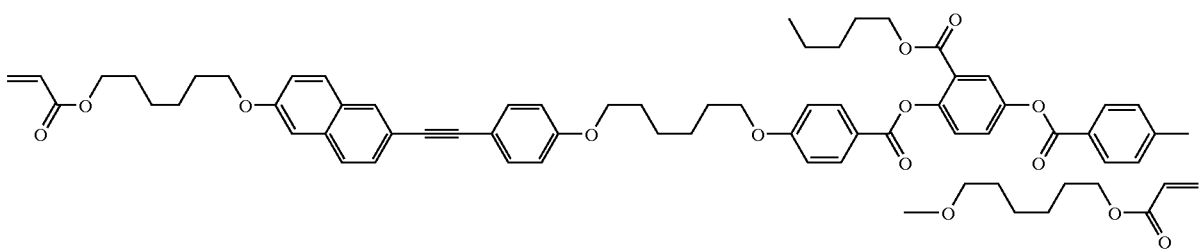
Iso. 162° C. N 23° C. K
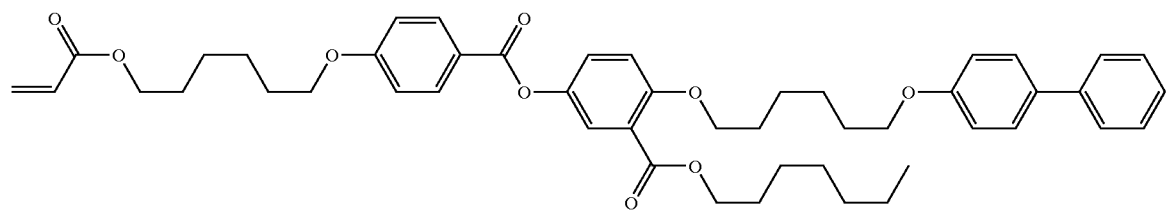
Iso. 55.8° C. N
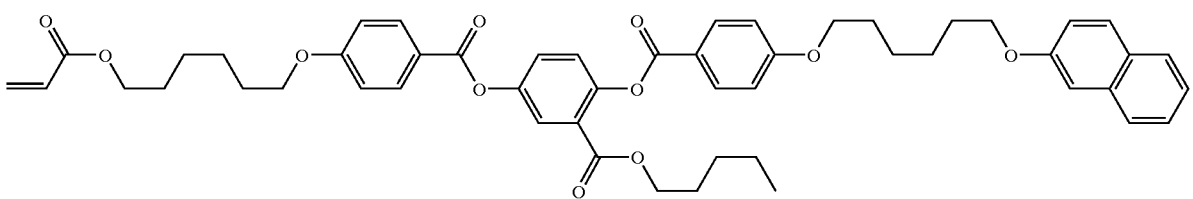
Iso. 118° C. N 48° C. S
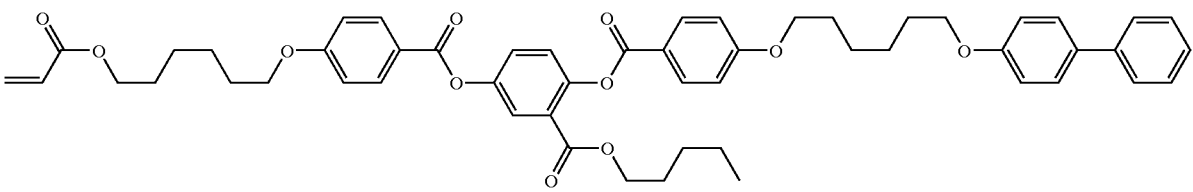
Iso. 121° C. N 37° C. K -continued
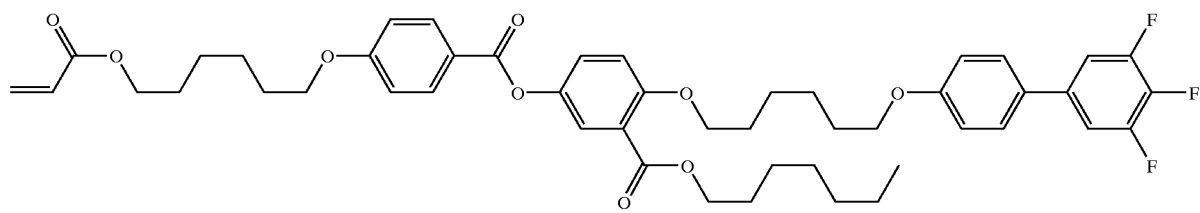
Iso. 45° C. N
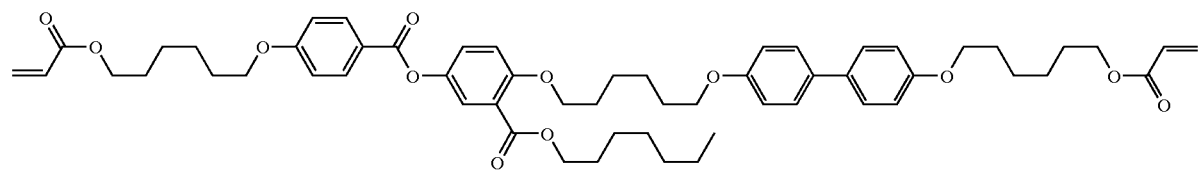
Iso. 36° C. N
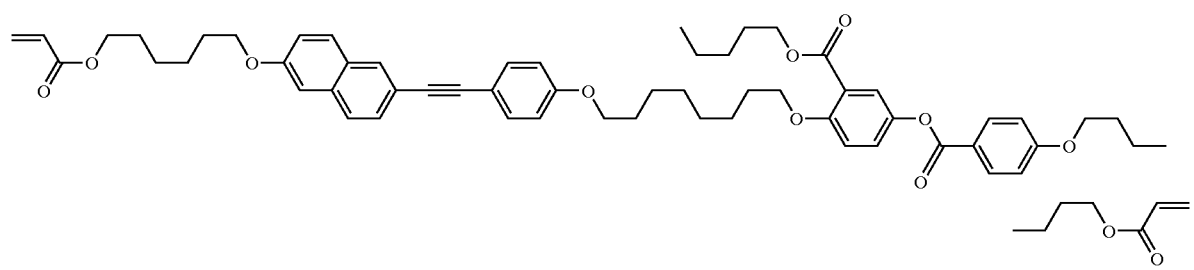
Iso. 104.8° C. N 23° C. K
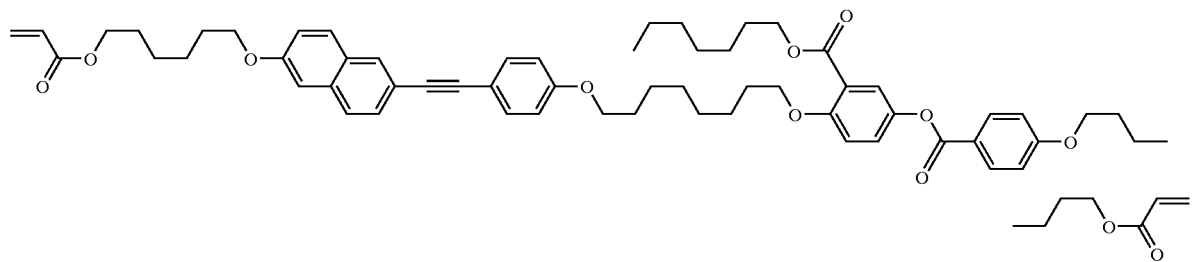
Iso. 102.6° C. N 23° C. K
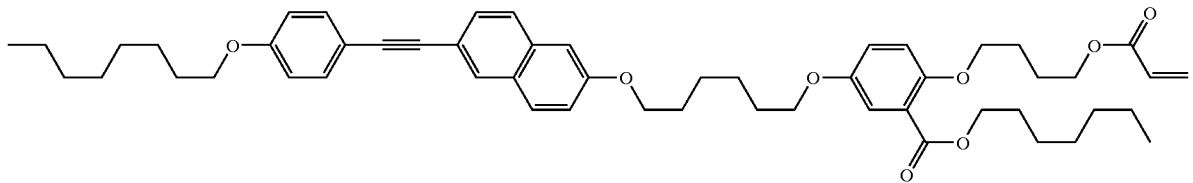
Iso. 90° C. N 75° C. S
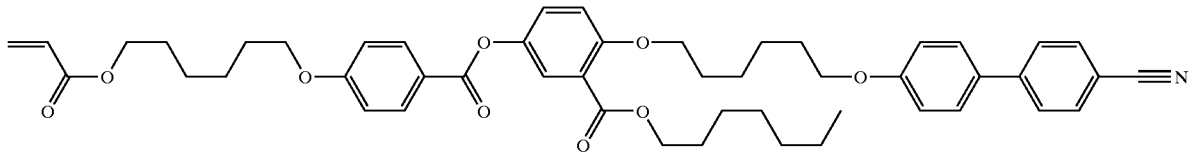
Iso. 86.5° C. N 23° C. K -continued
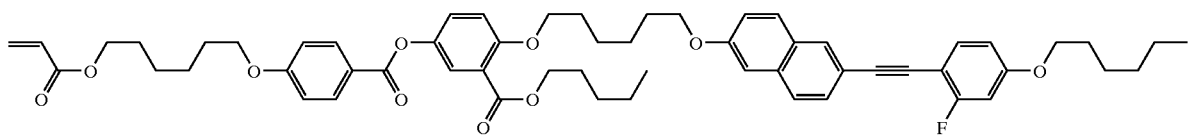
Iso. 118° C. N
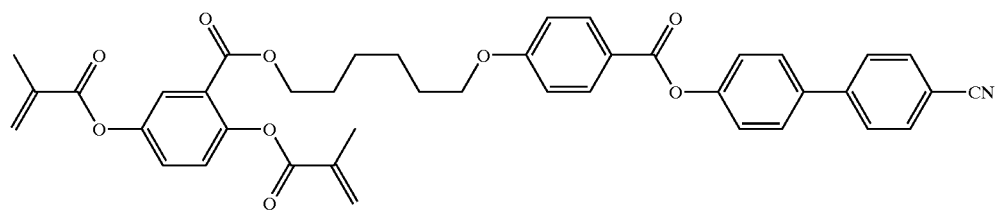
Iso. 114° C. N 23° C. K
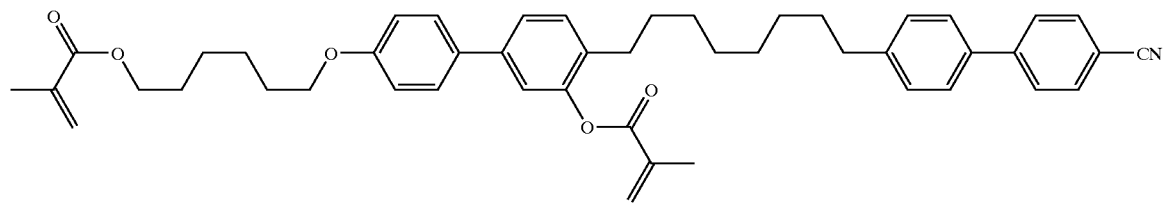
Iso. 83° C. N 60° C. K
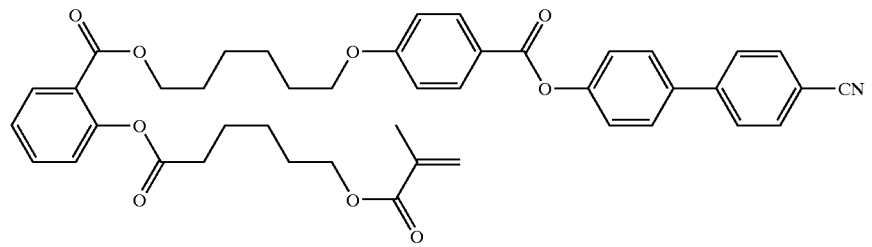
Iso. 84° C. N 33° C. $S_A$
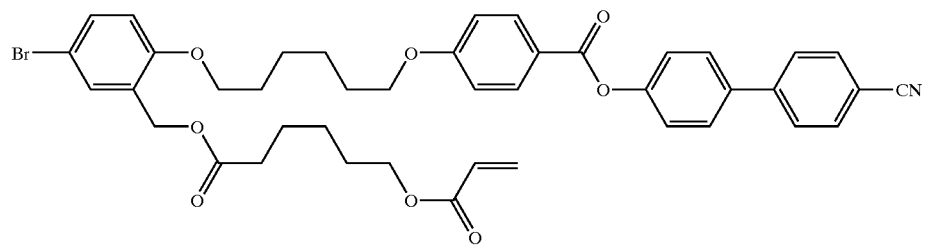
Iso. 84° C. N 33° C. $S_A$

EXAMPLE 7

400 mg of the following compound:

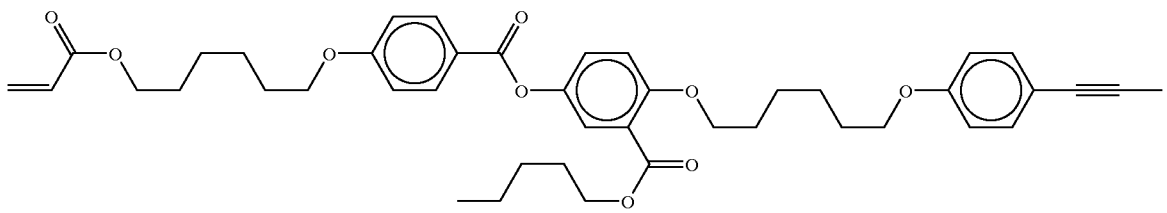

was mixed with 500 p.p.m. inhibitor 2,6-di-tert-butyl-4-methylphenol (BHT) to prevent premature polymerisation. For the radical photo-polymerisation 500 p.p.m. of an photoinitiator was added (IRGACURE™ 369 (commercially

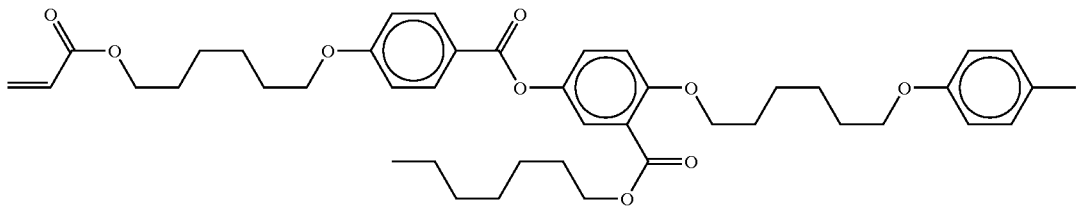

available from Ciba Geigy, Basle, Switzerland)). The resulting mixture was dissolved in anisole to a concentration of 20%.

The mixture was stirred at room temperature and spin-coated onto a glass plate with an upper orientation layer to form a layer of ca. 1000 nm. This film was dried at 80° C. for 1 or 2 minutes and photo-polymerised by irradiation with UV light using a Mercury lamp for 5 minutes at room temperature under a $N_2$ atmosphere.

The resulting film was essentially free of defects and exhibited a well-oriented nematic mesophase at room temperature. It has the following characteristics:

Film thickness: 1 μm
Clearing point: 110.9° C.
Δn : 0.22 (25° C.)
Tilt: 0°

EXAMPLE 8

Following the procedure of Example 7 a film was prepared using 400 mg of

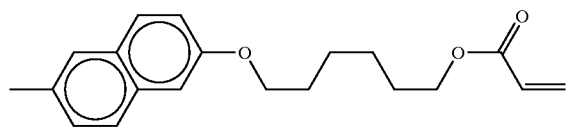

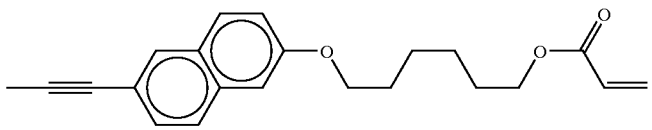

500 p.p.m. BHT 500 p.p.m. IRGACURE™ 369 in anisole with a ratio of 20:80.

The film was irradiated with UV light using Mercury lamp for 5 minutes at room temperature under a $N_2$ atmosphere. The resulting film was essentially free of defects and exhibited a well-oriented nematic mesophase at room temperature. It has the following characteristics:

Film thickness:1 μm
Clearing point: 105° C.
Δn : 0.23 (25° C.)
Tilt: 11°

EXAMPLE 9

Using the procedure of Example 7, a film was prepared from the following mixture:

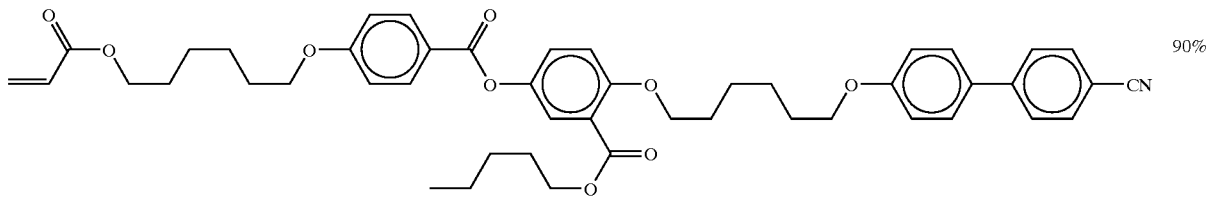
90%

1,4-butanediol diacrylate 10%

The resulting film was essentially free of defects and exhibited a well-oriented nematic mesophase at room temperature. It has the following characteristics:

Film thickness: 1 μm
Clearing point: 86.5° C.
Δn: 0.20 (25° C.)
Tilt: 1°

EXAMPLE 10

A mixture comprising

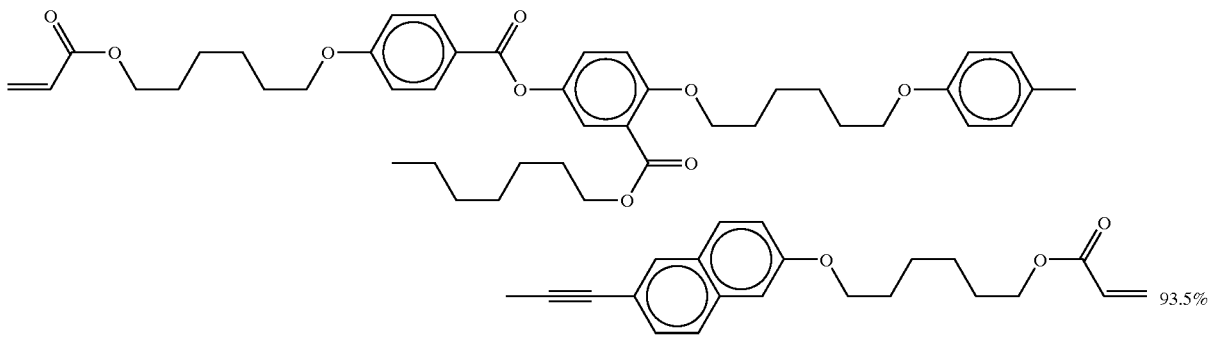

A (left handed) chiral component

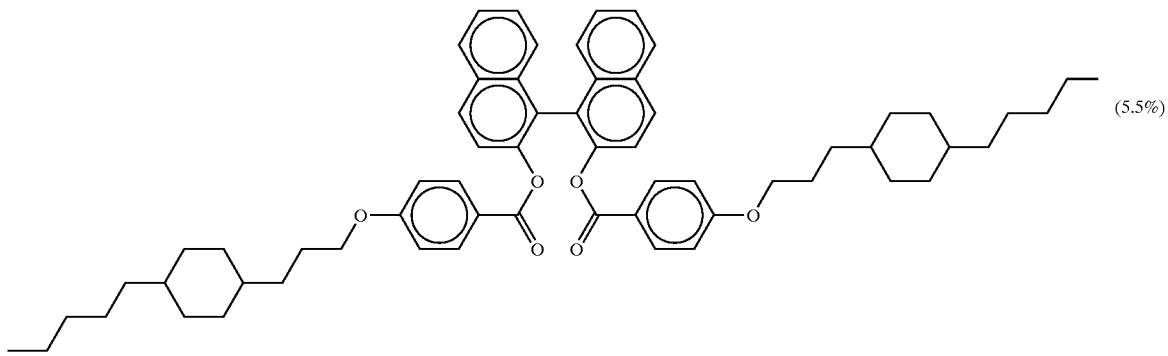
(5.5%)

500 ppm BHT and
500 ppm IRGACURE™ 369 was dissolved in anisol with a ratio of 40:60. The mixture was stirred at 60° C. and spin coated (600 Upm, 60 s) onto a glass substrate covered with a LPP/LCP orientation layer to form a layer of 4000 nm. The film was annealed at 85° C. for 15 minutes to give an essentially defect free film having a cholesteric planar orientation. It was then photo-polymerised using UV light (Hg lamp) at 85° C. for 5 minutes under an $N_2$ atmosphere.

The film was characterised by a strong reflection at around $\lambda_o$=610 nm, half-width=60 nm, excellent transparency outside the selective reflection band and good polarisation characteristics (extinction ratio for circular polarised light (left to right) better than 100:1)

EXAMPLE 11

A cholesteric mixture was prepared using the procedure of Example 10 using a right handed chiral component (5.5%).

The mixture was spin coated onto the cholesteric layer of example 10 using the procedure described above. The resulting double layer exhibited the characteristics of a notchfilter, blocking unpolarised light around $\lambda_o$=610 nm and having an extinction ratio better 150:1

What is claimed is:

1. A compound of formula I

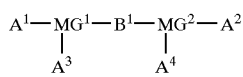
(I)

wherein $A^1$ to $A^4$ are independently selected from the group consisting of hydrogen, a methyl group and a hydrocarbon group containing from 2 to 80 carbon atoms in which one or more carbon atoms are optionally replaced by a heteroatom selected from the group consisting —O—, —S— and —N— and in which one or more hydrogen atoms are optionally substituted by a substituent selected from the group consisting of $C_{1-20}$ alkyl, $C_{2-20}$ alkenyl, $C_{2-20}$ alkynyl, amino, cyano, epoxy, halogen, hydroxy, nitro or oxo, with the proviso that firstly no two oxygen atoms are joined together and secondly that at least one of $A^1$ to $A^4$ includes a polymerisable group;

$B^1$ represents a hydrocarbon group containing from 4 to 80 carbon atoms, in which one or more carbon atoms are optionally replaced by a heteroatom selected from the group consisting of —O—, —S— and —N— and in which one or more hydrogen atoms are optionally substituted by a substituent selected from the group consisting of $C_{1-20}$ alkyl, $C_{2-20}$ alkenyl, $C_{2-20}$ alkynyl, amino, cyano, epoxy, halogen, hydroxy, nitro or oxo, with the proviso that no two oxygen atoms are joined together;

$MG^1$ and $MG^2$ each independently are selected from a group of formula (IV)

$$C^1-(Z^1-C^2)_{a1}-(Z^2-C^3)_{a2}-(Z^3-C^4)_{a3} \qquad (IV),$$

wherein $C^1$ to $C^4$ are each independently selected from the group consisting of an optionally substituted non-aromatic, aromatic, carbocyclic or heterocyclic group containing from 2 to 14 carbon atoms;

$Z^1$ to $Z^3$ are each independently selected from the group consisting of —CH(OH)—, —CO—, —CH$_2$(CO)—, —SO—, —CH$_2$(SO)—, —SO$_2$—, —CH$_2$(SO$_2$)—, —COO—, —OCO—, —COCF$_2$—, —CF$_2$CO—, —S—CO—, —CO—S—, —SOO—, —OSO—, —SOS—, —CH$_2$—CH$_2$—, —OCH$_2$—, —CH$_2$O—, —CH=CH—, —C≡C—, —CH=CH—COO—, —OCO—CH=CH— and a single bond; and a1, a2 and a3 are each independently 0 or an integer having a value of from 1 to 3, with the proviso that a1+a2+a3≦3, and with the proviso that firstly at least one of $MG^1$ and $MG^2$ comprises at least two ring systems and secondly when $MG^1$ and $MG^2$ are identical, either $A^1$ and $A^2$ or $A^3$ and $A^4$ are different or at least three of $A^1$ to $A^4$ are different, wherein groups $A^1$, $MG^1$, $B^1$, $MG^2$ and $A^2$ are linearly arranged with respect to each other.

2. A compound according to claim 1, in which at least one of the groups $A^1$ to $A^4$ comprise a group of formula (II)

(II)

wherein

P is hydrogen or a polymerisable group selected from the group consisting of CH$_2$=CW—, CH$_2$=CW—O—, CH$_2$=CW—COO—, CH$_2$=C(Ph)—COO—, CH$_2$=CH—COO—Ph—, CH$_2$=CW—CO—NH—, CH$_2$=C(Ph)—CONH—, CH$_2$=C(COOR')—CH$_2$—COO—, CH$_2$=CH—O—, CH$_2$=CH—OOC—, (Ph)—CH=CH—, CH$_3$—CH=N—(CH$_2$)$_{m3}$—, HO—, HS—, HO—(CH$_2$)$_{m3}$—, HS—(CH$_2$)$_{m3}$—, HO(CH$_2$)$_{m3}$COO—, HS(CH$_2$)$_{m3}$COO—, HWN—, HOC(O)—, CH2=CH—Ph—(O)$_{m4}$

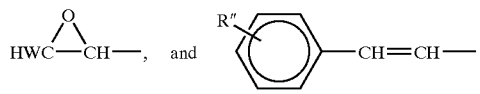

wherein

W is selected from the group consisting of H, F, Cl, Br, I and a $C_{1-5}$ alkyl group;

m3 is an integer having a value of from 1 to 9;

m4 is an integer having a value of 0 or 1,

R' represents a $C_{1-5}$ alkyl group; and

R" is selected from the group consisting of a $C_{1-5}$ alkyl group, methoxy, cyano, F, Cl, Br and I;

$Sp^1$ represents a $C_{1-20}$ alkylene group, which is optionally substituted by one or more substituents selected from the group consisting of F, Cl, Br, I, and CN, and in which one or more of the CH$_2$ groups present in the hydrocarbon chain are optionally replaced by one or more groups selected from the group consisting of —O—, —S—, —NH—, —N(CH$_3$)—, —CH(OH)—, —CO—, —CH$_2$(CO)—, —SO—, —CH$_2$(SO)—, —SO$_2$—, —CH$_2$(SO$_2$)—, —COO—, —OCO—, —OCO—O—, —S—CO—, —CO—S—, —SOO—, —OSO—, —SOS—, —SF$_5$—, —C≡C—, —(CF$_2$)$_r$—, —(CD$_2$)$_s$—, —(CCl$_2$)$_s$—, and C(W$^1$)=C(W$^2$)—, wherein W$^1$ and W$^2$ are each independently selected from the group consisting of H, H—(CH$_2$)$_{q1}$— and Cl, with the proviso that no two heteroatoms are joined together and wherein the integers r, s and q1 independently represent a number of from 1 to 15;

k1 is an integer having a value of from 0 to 4;

$X^1$ is selected from the group consisting of —O—, —S—, —NH—, —N(CH$_3$)—, —CH(OH)—, —CO—, —CH$_2$(CO)—, —SO—, —CH$_2$(SO)—, —SO$_2$—, —CH$_2$(SO$_2$)—, —COO—, —OCO—, —OCO—O—, —S—CO—, —CO—S—, —SOO—, —OSO—, —SOS—, —CH$_2$—CH$_2$—, —OCH$_2$—, —CH$_2$O—, —CH=CH— and —C≡C—; and t1 is an integer having a value of 0 or 1.

3. A compound according to claim 2, in which k1 and t1 each have a value of 1.

4. A compound according to claim 2, in which $X^1$ is selected from the group consisting of —O—, —COO—, and —OCO—.

5. A compound according to claim 2, in which $Sp^1$ is selected from the group consisting of ethylene, propylene, butylene, pentylene, hexylene, heptylene, octylene, nonylene, decylene, undecylene, and dodecylene.

6. A compound according to claim 1, in which $B^1$ is a group of formula (III)

$$(X^2)_{t2}—Sp^2—(X^3)_{t3} \quad (III)$$

wherein

Sp$^2$ represents a C$_{4-20}$ alkylene group, in which one or more carbon atoms are optionally replaced by a heteroatom selected from the group consisting of —O— and —N— with the proviso that no two heteroatoms are joined together;

X$^2$ and X$^3$ are each independently selected from the group consisting of —O—, —S—, —NH—, —N(CH$_3$)—, —CH(OH)—, —CO—, —CH$_2$(CO)—, —SO—, —CH$_2$(SO)—, —SO$_2$—, —CH$_2$(SO$_2$)—, —COO—, —OCO—, —OCO—O—, —S—CO—, —CO—S—, —SOO—, —OSO—, —SOS—, —CH$_2$—CH$_2$—, —OCH$_2$—, —CH$_2$O—, —CH=CH—, —C≡C— and a single bond; and t2 and t3 each independently have a value of 0 or 1.

7. A compound according to claim 6, in which X$^2$ and X$^3$ are each independently selected from the group consisting of —O—, —COO—, —OCO— and a single bond.

8. A compound according to claim 6, in which Sp$^2$ is selected from the group consisting of butylene, pentylene, hexylene, heptylene, octylene, nonylene, decylene, undecylene and dodecylene.

9. A compound according to claim 1, in which the groups C$^1$ to C$^4$ are each independently selected from the group consisting of

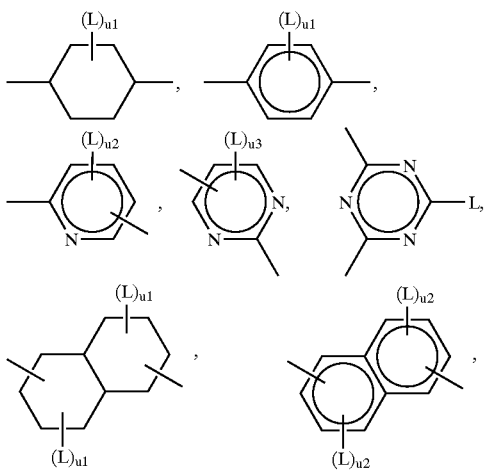

-continued

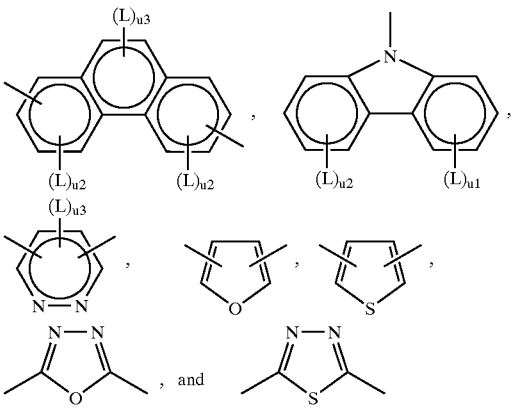

wherein

L is selected from the group consisting —C$_n$H$_{2n+1}$, —C(O)C$_n$H$_{2n+1}$, —C(O)OC$_n$H$_{2n+1}$, —OC(O)C$_n$H$_{2n+1}$, —OC$_n$H$_{2n+1}$, —NO$_2$, —CN, —SF$_5$ and halogen;

n represents an integer having a value of from 1 to 20;

u1 represents 0 or an integer having a value of from 1 to 4;

u2 represents 0 or an integer having a value of from 1 to 3; and u3 represents 0 or an integer having a value of from 1 to 2.

10. A compound according to claim 1, in which C$^1$ to C$^4$ are each independently selected from the group consisting of cyclohexyl, cyclohexylene, phenyl, phenylene, naphthyl, naphthylene, phenanthryl, phenanthrylene, decalinyl and decalinylene.

11. A liquid crystalline mixture comprising at least two components, in which at least one component comprises a compound of formula (I) according to claim 1.

12. A liquid crystalline material comprising a compound of formula (I) according to claim 1.

13. A liquid crystalline material according to claim 12, in the form of a polymer network.

14. An optical or an electro-optical device, comprising a compound of formula (I) according to claim 1.

15. An optical or electro-optical device comprising a liquid crystalline material according to claim 12 in monomeric, polymeric or polymer network form.

* * * * *

UNITED STATES PATENT AND TRADEMARK OFFICE
CERTIFICATE OF CORRECTION

PATENT NO. : 6,746,729 B1
DATED : June 8, 2004
INVENTOR(S) : Zoubair Mohammed Cherkaoui et al.

It is certified that error appears in the above-identified patent and that said Letters Patent is hereby corrected as shown below:

Column 43,
Line 24, after "consisting", insert -- of --.

Column 44,
Line 49, "sand" should read -- s and --.

Column 46,
Line 21, after "consisting", insert -- of --.

Signed and Sealed this

Twenty-second Day of March, 2005

JON W. DUDAS
*Director of the United States Patent and Trademark Office*